(12) United States Patent
Miyadera et al.

(10) Patent No.: US 11,857,513 B2
(45) Date of Patent: Jan. 2, 2024

(54) SELECTIVE INHIBITOR OF EXON 20 INSERTION MUTANT EGFR

(71) Applicant: Taiho Pharmaceutical Co., Ltd., Tokyo (JP)

(72) Inventors: Kazutaka Miyadera, Tsukuba (JP); Yoshimi Aoyagi, Tsukuba (JP); Shinichi Hasako, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 16/345,792

(22) PCT Filed: Oct. 31, 2017

(86) PCT No.: PCT/JP2017/037186
§ 371 (c)(1),
(2) Date: Apr. 29, 2019

(87) PCT Pub. No.: WO2018/079310
PCT Pub. Date: May 3, 2018

(65) Prior Publication Data
US 2019/0262345 A1  Aug. 29, 2019

(30) Foreign Application Priority Data

Oct. 31, 2016 (JP) ................ 2016-213072

(51) Int. Cl.
*A61K 31/519* (2006.01)
*A61P 35/00* (2006.01)

(52) U.S. Cl.
CPC ............ *A61K 31/519* (2013.01); *A61P 35/00* (2018.01)

(58) Field of Classification Search
CPC .............................. A61K 31/519; A61P 35/00
See application file for complete search history.

(56) References Cited

U.S. PATENT DOCUMENTS

| | | | |
|---|---|---|---|
| 5,733,918 A | 3/1998 | Okazaki et al. | |
| 8,119,142 B2 | 2/2012 | Zwijsen et al. | |
| 8,889,666 B2 | 11/2014 | Sagara et al. | |
| 8,912,181 B2 | 12/2014 | Kitade et al. | |
| 2014/0057899 A1 | 2/2014 | Sagara et al. | |
| 2014/0343038 A1 | 11/2014 | Sakamoto et al. | |
| 2014/0378409 A1 | 12/2014 | Fujita et al. | |
| 2016/0194332 A1 | 7/2016 | Uno et al. | |
| 2017/0101414 A1 | 4/2017 | Uno et al. | |
| 2020/0253975 A1 | 8/2020 | Abe et al. | |

FOREIGN PATENT DOCUMENTS

| | | |
|---|---|---|
| CN | 1130903 A | 9/1996 |
| CN | 102471335 A | 5/2012 |
| CN | 105683195 A | 6/2016 |
| EP | 2722332 A1 | 4/2014 |
| EP | 2960241 A1 | 12/2015 |
| EP | 3037424 A1 | 6/2016 |
| JP | 2008-533172 A | 8/2008 |
| JP | 2016-213072 A | 12/2016 |
| KR | 10-2016-0043114 A | 4/2016 |
| WO | WO-2006/102079 A1 | 9/2006 |
| WO | WO-2011/046964 A2 | 4/2011 |
| WO | WO-2012/093708 A1 | 7/2012 |
| WO | WO-2013/047813 A1 | 4/2013 |
| WO | WO-2013/100014 A1 | 7/2013 |
| WO | WO-2013/118817 A1 | 8/2013 |
| WO | WO-2013/125709 A1 | 8/2013 |
| WO | WO-2014/129596 A1 | 8/2014 |
| WO | WO-2015/025936 A1 | 2/2015 |
| WO | WO-2015/175632 A1 | 11/2015 |
| WO | WO-2015/195228 A1 | 12/2015 |

OTHER PUBLICATIONS

Sasaki (EGFR exon 20 insertion mutation in Japanses lung cancer, Lung Cancer (2007) 58, 324-328).*
Oxnard (Natural history and molecular characteristics of lung cancers harboring EGFR exon 20 insertions, Thorac Oncol. Feb. 2013 ; 8(2): 179-184).*
Arteaga "The Epidermal Growth Factor Receptor: From Mutant Oncogene in Nonhuman Cancers to Therapeutic Target in Human Neoplasia", Journal of Clinical Oncology, 2001, vol. 19, No. 18s, pp. 32s-40s.
Chong et al. "The quest to overcome resistance to EGFR-targeted therapies in cancer" Nature Medicine, vol. 19, pp. 1389-1400 (2013).
Doebele et al., "New strategies to overcome limitations of reversible EGFR tyrosine kinase inhibitor therapy in non-mall cell lung cancer", Lung Cancer, 2010, vol. 69, No. 1, pp. 1-12.
Hirano et al. "In vitro modeling to determine mutation specificity of EGFR tyrosine kinase inhibitors against clinically relevant EGFR mutants in non-small-cell lung cancer", Oncotarget, 2015, 6(36):38789-38803.
International Search Report for PCT/JP2017/037186 dated Dec. 19, 2017.
Jia et al. "EGF816 Exerts Anticancer Effects in Non-Small Cell Lung Cancer by Irreversibly and Selectively Targeting Primary and Acquired Activating Mutations in the EGF Receptor", Cancer Research, 2016, 76(6):1591-1602.
Lacouture, Mario E. "Mechanisms of cutaneous toxicities to EGFR inhibitors" Nat. Rev. Cancer, vol. 6, pp. 803-812 (2006).
Li et al. "Design and implementation of the MMC simulation system in the heterogeneous FPGA-CPU platform" Lancet Oncol. vol. 13, e. 23-31 (2012).

(Continued)

*Primary Examiner* — Kathrien A Hartsfield
(74) *Attorney, Agent, or Firm* — Oblon, McClelland, Maier & Neustadt, L.L.P.

(57) ABSTRACT

An antitumor agent comprising a compound selected from the group consisting of Compounds A to D described in the specification, or a salt thereof, for treating a malignant tumor patient expressing EGFR having exon 20 insertion mutation.

9 Claims, 15 Drawing Sheets
Specification includes a Sequence Listing.

(56) References Cited

OTHER PUBLICATIONS

Ministry of Internal Affairs and Communications Statistics Bureau homepage I statistical data / world statistics "World Statistics 2011", p. 332 14-1.

Naidoo et al. "EGFRexon 20 insertions in advanced lung adenocarcinomas: clinical outcomes and response to erlotinib" Cancer. Sep. 15, 2015; 121(18): 3212-3220.

Naidoo et al.: Epidermal growth factor receptor exon 20 insertions in advanced lung adenocarcinomas: Clinical outcomes and response to erlotinib : EGFR Exon 20 Insertions11, Cancer., vol. 121, No. 18, Jun. 10, 2015 (Jun. 10, 2015), pp. 3212-3220.

Pao et al., "Rational, biologically based treatment of EGFR-mutant non-small-cell lung cancer", Nature Reviews Cancer, 2010, vol. 10, No. 11, pp. 760-774.

Sharma et al."Epidermal growth factor receptor mutations in lung cancer" Nat. Rev. Cancer, vol. 7, pp. 169-181 (2007).

Yang et al. Clinical activity of afatinib in patients with advanced non-small-cell lung cancer harbouring uncommon EGFR mutations: a combined post-hoc analysis of LUX-Lung 2, LUX-Lung 3, and LUX-Lung 6; Lancet Oncol. vol. 16, pp. 830-838 (2015).

Yasuda et al. "EGFR exon 20 insertion mutations in non-small-cell lung cancer: preclinical data and clinical implications" The medical frontline, 2011, Lancet Oncol 2012; 13: e23-31.

Yasuda et al. "Structual, Biochemical, and Clinical Characterization of Epidermal Growth Factor Receptor (EGFR) Exon 20 Insertion Mutations in Lung Cancer", Science Translational Medicine, 2013, 5(214-216):135-144.

Yasuda, Hiroyuki "EGFR Exon 20 Insertion Mutations in Lung Cancer" Aug. 2016, vol. 71, No. 8, pp. 1721-1725.

International Search Report for PCT/JP2018/032314 dated Oct. 30, 2018.

Kobayashi et al. "Not all epidermal growth factor receptor mutations in lung cancer are created equal: Perspectives for individualized treatment strategy," Cancer Sci., 2016, 107(9):1179-86.

Nishino, K., et al. "Guidelines of examination about EGFR gene mutations in lung cancer patient," ver. 3. 05, [online], 2016, [retrieval date Feb. 25, 2020], internet<URL:https://haigan.gr.jp/uploads/files/photos/1329.pdf>, machine translation.

Yang et al. "Clinical activity of afatinib in patients with advanced non-small-cell lung cancer harbouring uncommon EGFR mutations: a combined post-hoc analysis of LUX-Lung 2, LUX-Lung 3, and LUX-Lung 6," Lancet Oncol., 2015, 16(7):830-8.

International Preliminary Report on Patentability for PCT/JP2019/051377, dated Jul. 8, 2021, 8 pages.

Wei, Y., et al., "Three new disease-progression modes in NSCLC patients after EGFR-TKI treatment by next-generation sequencing analysis", Lung Cancer, Elsevier, vol. 125, Sep. 1, 2018, pp. 43-50.

Piotrowska et al., "Preliminary Safety and Activity of CLN-081 in NSCLC with EGFR Exon 20 Insertion Mutations (Ins20)", EMSO2020 Poster, 2020, 1 page.

Piotrowska et al., "Abstract 9077: Safety and activity of CLN-081 (TAS6417) in NSCLC with EGFR Exon 20 insertion mutations (Ins20)", ASCO Poster, 2021, 5 pages.

Kye Young Lee, "Molecular diagnosis in lung cancer", J. Lung Cancer, 2010, 9(1), pp. 9-14.

Request for Submission of an Opinion of Korean Patent Application No. 10-2019-7015270 dated Oct. 4, 2022 (with English Translation), 14 pages.

* cited by examiner

Fig. 15

```
Wild-type EGFR (Accession number NP_005219.2)
   1 mrpsgtagaa llallaalcp asraleekkv cqtsnkltq  lgtfedhfls  lqrmfnncev
  61 vlgnleityv qrnydlsflk tlqevagyvl lalntverlp  lenlqllrgn  myyensyala
 121 vlsnydankt glkelpmrnl qellhgavrf snnpalcnve  slqwrdlvss  dflsnmsmdf
 181 qnhlgscqkc dpscpngscw gageencqkl tklicaqqcs  grcrgkspsd  cchnqcaagc
 241 tgpresdclv crkfrdeatc kdtppimly nptty gmdvn   pegkysfgat  cvkkcprnyv
 301 vtdhgscvra cgadsyemee dgvrkckkce  gpcrkvcngi  gigefkdsls  inatnikhfk
 361 nctsisgdlh ilpvafrgds fthtppldpq  eldilktvke  itgflliqaw  penrtdlhaf
 421 enleilrgrt kqhgqfslav vslnitslgl  rslkeisdgd  viisgnknlc  yantinwkkl
 481 fgtsgqktki  isnrgensck atgqvchalc  spegcwgpep  rdcvscrnvs  rgrecvdkcn
 541 llegeprefv enseclqchp ecipqamnit  ctgrgpdnci  qcahyidgph  cvktcpagvm
 601 genntlvwky adaghvchlc hpnctygctg  pglegcptng  pklpslatgm  vgalllllvv
 661 algiglfmrr rhivrkrtlr rllqerelve  pltpsgeapn  qallriket   efkklkvlgs
 721 gafgtvykgl wlpegekvkl qlmpfgclld  pvaikelrea  tspkankell  deaymasvd   nphvcrllgi
 781 cltstvqlit qlmpfgclld yvrehkdnig  sqyllnwcvq  lakgmnyled  rrlvhrdlaa
 841 rnvlktpqh  vkltdfglak llgaeekeyh  aeggkvpikw  malesilhri  ythqsdvwsy
 901 gvtvwelmtf gskpydgipa selssilekg  erlpqplct   idvymimvkc  wmidadsrpk
 961 frellefsk  mardparylv lqgdermhlp  sptdsnfyra  lmdeedmddv  vdadeylipq
1021 qgffsspsts rtplissa   tsnnstvaci  drnglqscpi  kedsflqrys  sdptgalted
1081 siddtflpvp eylrqsvpkr pagsvqnpvy  hnqplnpaps  rdphyqdphs  tavgnpeyln
1141 tvaptcvnst fdspahwaqk gshqisldnp  dyqqdffpke  akpngifkgs  taenaeylrv
1201 apqssefiga
```

SELECTIVE INHIBITOR OF EXON 20 INSERTION MUTANT EGFR

CROSS REFERENCE TO RELATED APPLICATION

This application is a United States National Phase Application under 35 U.S.C. § 371 of International Application PCT/JP2017/037186 filed on Oct. 31, 2017, which claims priority from Application 2016-213072 filed on Oct. 31, 2016 in Japan. The entire contents of each these applications are incorporated herein by reference in their entirety.

TECHNICAL FIELD

The present invention relates to an antitumor agent against cancers, comprising an exon 20 insertion mutant epidermal growth factor receptor (hereinafter referred to as "EGFR").

BACKGROUND ART

EGFR is a receptor-type tyrosine kinase, exerts its physiological function in normal tissue by being bound to Epidermal Growth Factor (hereinafter also referred to as EGF), which is a ligand, and contributes to growth and apoptosis inhibition in epithelial tissues (NPL 1). Further, somatic mutation of EGFR gene has been known as a cancer-causing gene; for example, EGFR in which the 746th to 750th amino acids in the exon 19 region are deleted (hereinafter also referred to as "exon 19 deletion mutation") and EGFR in which the 858th amino acid in the exon 21 region is mutated from leucine to arginine (hereinafter also referred to as "L858R mutation") constantly induces EGF-independent kinase activity, and contributes to the growth and survival of cancer cells (NPL 2). These mutations are observed, for example, in 30 to 50% of non-small-cell lung cancer in East Asia. The mutations are also observed in about 10% of non-small-cell lung cancer in Europe and the United States, and is regarded as one of the causes of cancers (NPL 3).

Therefore, research and development of EGFR inhibitor as an antitumor agent have actively been conducted, and introduced into the treatment of EGFR mutation-positive lung cancer. For example, although administration of gefitinib, erlotinib, and afatinib in their therapeutic dose causes, as side effects, digestive tract disorders and skin disorders, which are widely thought to be attributable to inhibition of wild-type EGFR, they exert a high antitumor effect against exon 19 deletion mutant and L858R mutant EGFR-positive lung cancers. The therapeutic effects of these agents are assumed to be derived from selective inhibition against mutant EGFR, compared with wild-type EGFR, by an EGFR inhibitor (NPL 4).

However, recent studies found that some cancers have EGFR with a mutation in which one or more amino acids are inserted in the exon 20 region (hereinafter also referred to as "exon 20 insertion mutation"), and that these cancers have low sensitivity with respect to previously known EGFR inhibitors. For example, there are clinical reports showing significantly lower antitumor effects of afatinib against EGFR mutation-positive lung cancer with respect to exon 20 insertion mutation, compared with exon 19 deletion mutation or L858R mutation (NPL 5). For this reason, chemotherapies have been used for the patients with these cancers. However, since the treatment options are limited and sufficient therapeutic effects have not been obtained, an antitumor agent with further higher therapeutic effects has been demanded.

PTL 1 discloses a compound usable for the treatment of diseases characterized by exon 20 insertion mutant EGFR. However, the compound of PTL 1 greatly differs in its structure from the compound according to the present invention, and PTL 1 nowhere discloses selectivity based on a comparison with wild-type EGFR, or efficacy in an in vivo model.

Further, although PTL 2 discloses a quinoline-substituted compound, PTL 2 nowhere discloses inhibitory activity against exon 20 insertion mutant EGFR.

CITATION LIST

Patent Literature

PTL 1: WO2015/175632A1
PTL 2: WO2015/025936A1

Non-Patent Literature

NPL 1: Nat. Rev. Cancer, Vol. 6, pp. 803-812 (2006)
NPL 2: Nature Medicine, Vol. 19, pp. 1389-1400 (2013)
NPL 3: Nat. Rev. Cancer, Vol. 7, pp. 169-181 (2007)
NPL 4: Lancet Oncol. Vol. 13, e. 23-31 (2012)
NPL 5: Lancet Oncol. Vol. 16, pp. 830-838 (2015)

SUMMARY OF INVENTION

Technical Problem

An object of the present invention is to provide an antitumor agent with reduced side effects derived from the inhibition of wild-type EGFR, the antitumor agent serving as an inhibitor that can ensure high selectivity with respect to exon 20 insertion mutant EGFR for which the therapeutic effects of the previously known EGFR inhibitors are insufficient.

Solution to Problem

The inventors of the present invention conducted extensive research, and found that exon 20 insertion mutant EGFR is an appropriate target in treating cancers, and that EGFR inhibitors conventionally used for the treatments have inferior selectivity between wild-type EGFR and exon 20 insertion mutant EGFR. Further, the inventors also confirmed that a specific compound exerts selectivity with respect to exon 20 insertion mutant EGFR and tumor growth inhibitory effects, and is thus regarded as superior to afatinib, which is a typical EGFR mutation-positive cancer-treating agent. With this finding, the inventors accomplished the present invention.

Accordingly, the present invention encompasses the following embodiments.

Item 1.

An antitumor agent for treating a malignant tumor patient expressing EGFR having exon 20 insertion mutation, the antitumor agent comprising a compound selected from the group consisting of:

(S)—N-(4-amino-6-methyl-5-(quinolin-3-yl)-8,9-dihydropyrimido[5,4-b]indolizin-8-yl)acrylamide (hereinafter also referred to as Compound A);

(S)—N-(4-amino-6-methylene-5-(quinolin-3-yl)-7,8-di-
hydro-6H-pyrimido[5,4-b]pyrrolizin-7-yl) acrylamide
(hereinafter also referred to as Compound B);
(S,E)-N-(4-amino-6-methylene-5-(quinolin-3-yl)-7,8-di-
hydro-6H-pyrimido[5,4-b]pyrrolizin-7-yl)-3-chloroacryl-
amide (hereinafter also referred to as Compound C); and
(R)—N-(4-amino-6-methyl-5-(quinolin-3-yl)-8,9-dihydro-
pyrimido[5,4-b]indolizin-8-yl)-N-meth ylacrylamide
(hereinafter also referred to as Compound D), or a salt
thereof.

Item 2.

The antitumor agent according to Item 1, wherein the compound is (S)—N-(4-amino-6-methyl-5-(quinolin-3-yl)-8,9-dihydropyrimido[5,4-b]indolizin-8-yl)acrylamide.

Item 3.

The antitumor agent according to Item 1 or 2, wherein the malignant tumor patient expressing EGFR having exon 20 insertion mutation is a patient with lung cancer, breast cancer, head and neck cancer, brain tumor, uterine cancer, hematopoietic tumor, or skin cancer.

Item 4.

The antitumor agent according to any one of Items 1 to 3, wherein the malignant tumor patient expressing EGFR having exon 20 insertion mutation is a lung cancer patient.

Item 5.

The antitumor agent according to any one of Items 1 to 4, wherein the exon 20 insertion mutation is a mutation in which one or more amino acids are inserted in the exon 20 region.

Item 6.

The antitumor agent according to any one of Items 1 to 5, wherein the exon 20 insertion mutation is a mutation in which 1 to 7 amino acids are inserted in the exon 20 region.

Item 7.

The antitumor agent according to any one of Items 1 to 6, wherein the exon 20 insertion mutation is a mutation in which 1 to 4 amino acids are inserted in the exon 20 region.

Item 8.

The antitumor agent according to any one of Items 1 to 7, wherein the exon 20 insertion mutation is A763_Y764insFQEA, V769_D770insASV, D770_N771insSVD, D770_N771insNPG, D770_N771insG, D770>GY, N771_P772insN, P772_R773insPR, H773_V774insNPH, H773_V774insPH, H773_V774insAH, H773_V774insH, V774_C774insHV, or A761_E762insEAFQ.

Item 9.

The antitumor agent according to any one of Items 1 to 8, wherein the exon 20 insertion mutation is V769_D770insASV, D770_N771insSVD, D770_N771insG, H773_V774insNPH, or H773_V774insPH.

Item 10.

A method for treating a malignant tumor patient, comprising the step of administering an antitumor agent comprising an effective amount of a compound selected from the group consisting of:
(S)—N-(4-amino-6-methyl-5-(quinolin-3-yl)-8,9-dihydro-
pyrimido[5,4-b]indolizin-8-yl)acrylamide;
(S)—N-(4-amino-6-methylene-5-(quinolin-3-yl)-7,8-di-
hydro-6H-pyrimido[5,4-b]pyrrolizin-7-yl) acrylamide;
(S,E)—N-(4-amino-6-methylene-5-(quinolin-3-yl)-7,8-di-
hydro-6H-pyrimido[5,4-b]pyrrolizin-7-yl)-3-chloroacryl-
amide; and
(R)—N-(4-amino-6-methyl-5-(quinolin-3-yl)-8,9-dihydro-
pyrimido[5,4-b]indolizin-8-yl)-N-meth ylacrylamide,
or a salt thereof, to a malignant tumor patient expressing EGFR having exon 20 insertion mutation.

Item 11.

A compound selected from the group consisting of:
(S)—N-(4-amino-6-methyl-5-(quinolin-3-yl)-8,9-dihydro-
pyrimido[5,4-b]indolizin-8-yl)acrylamide;
(S)—N-(4-amino-6-methylene-5-(quinolin-3-yl)-7,8-di-
hydro-6H-pyrimido[5,4-b]pyrrolizin-7-yl) acrylamide;
(S,E)—N-(4-amino-6-methylene-5-(quinolin-3-yl)-7,8-di-
hydro-6H-pyrimido[5,4-b]pyrrolizin-7-yl)-3-chloroacryl-
amide; and
(R)—N-(4-amino-6-methyl-5-(quinolin-3-yl)-8,9-dihydro-
pyrimido[5,4-b]indolizin-8-yl)-N-meth ylacrylamide,
or a salt thereof, to treat a malignant tumor patient expressing EGFR having exon 20 insertion mutation.

Item 12.

Use of a compound selected from the group consisting of:
(S)—N-(4-amino-6-methyl-5-(quinolin-3-yl)-8,9-dihydro-
pyrimido[5,4-b]indolizin-8-yl)acrylamide;
(S)—N-(4-amino-6-methylene-5-(quinolin-3-yl)-7,8-di-
hydro-6H-pyrimido[5,4-b]pyrrolizin-7-yl) acrylamide;
and
(S,E)—N-(4-amino-6-methylene-5-(quinolin-3-yl)-7,8-di-
hydro-6H-pyrimido[5,4-b]pyrrolizin-7-yl)-3-chloroacryl-
amide; and
(R)—N-(4-amino-6-methyl-5-(quinolin-3-yl)-8,9-dihydro-
pyrimido[5,4-b]indolizin-8-yl)-N-methylacrylamide,
or a salt thereof for the production of an antitumor agent for treating a malignant tumor patient expressing EGFR having exon 20 insertion mutation.

Advantageous Effects of Invention

The antitumor agent of the present invention exerts high selectivity with respect to exon 20 insertion mutant EGFR without inhibiting wild-type EGFR. Therefore, the antitumor agent of the present invention is useful in view of providing an antitumor agent that has reduced side effects derived from the inhibition of wild-type EGFR; and that exerts superior therapeutic effects for a malignant tumor patient expressing EGFR having exon 20 insertion mutation, for which the therapeutic effects of the previously known EGFR inhibitors are insufficient.

The previously known EGFR inhibitors have low selectivity with respect to exon 20 insertion mutant EGFR, compared with wild-type EGFR; therefore, the difference between the dosage for ensuring the antitumor effects and the dosage causing the side effects (skin disorders, digestive tract disorders, etc.) derived from wild-type EGFR inhibition was small. Accordingly, the previously known EGFR inhibitors have difficulty in exerting sufficient therapeutic effects. In contrast, since the antitumor agent of the present invention has high selectivity with respect to exon 20 insertion mutant EGFR, it is possible to increase the dosage without causing side effects derived from wild-type EGFR. Therefore, the antitumor agent of the present invention exerts superior therapeutic effects for a malignant tumor patient expressing EGFR having exon 20 insertion mutation.

BRIEF DESCRIPTION OF DRAWINGS

FIG. 15 illustrates the amino acid sequence of wild-type EGFR (SEQ ID NO: 1).

DESCRIPTION OF EMBODIMENTS

Figure 1:
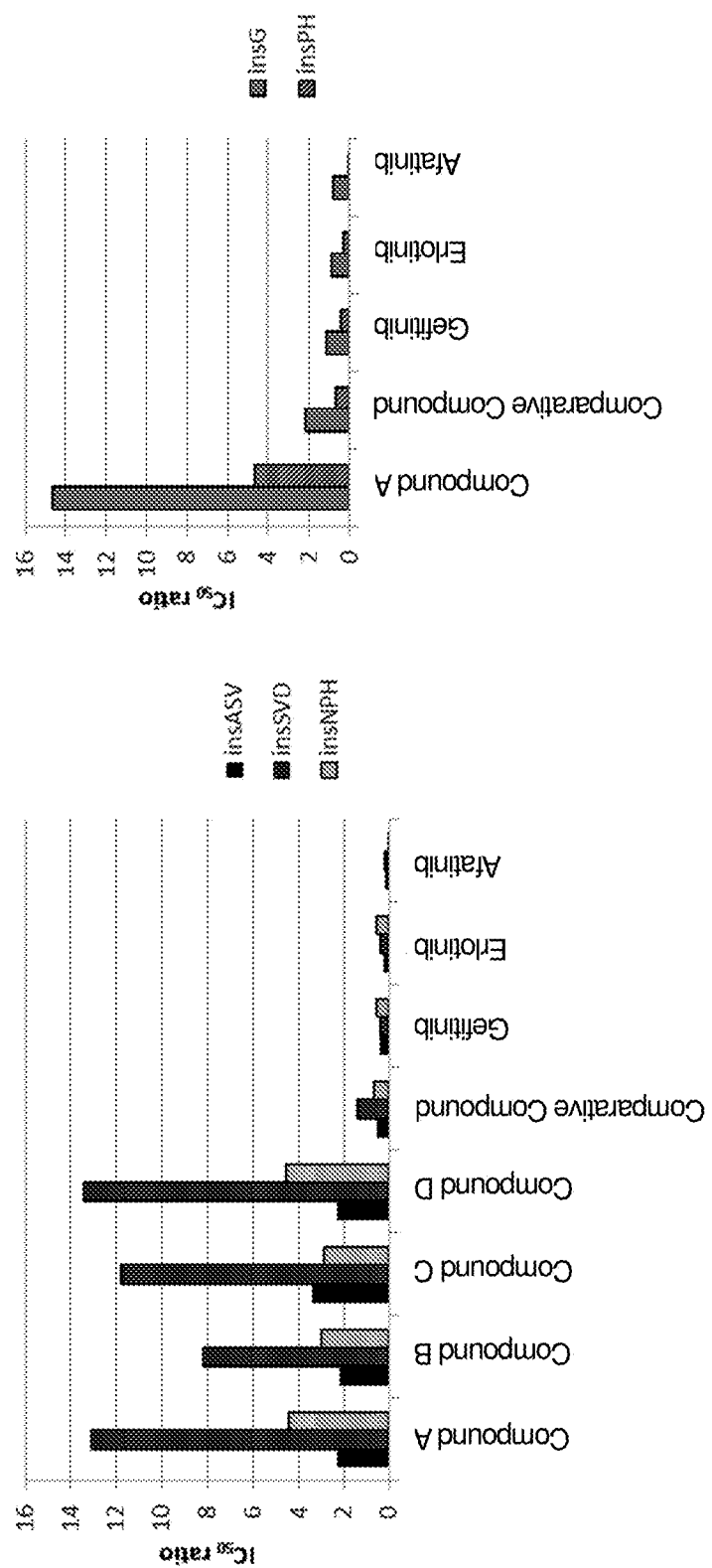
FIG. 1 illustrates $IC_{50}$ ratios of wild-type EGFR to EGFR exon 20 insertion mutations calculated from the results of a test for cell growth inhibition on wild-type EGFR-expressing cell lines and mutant EGFR-expressing cell lines by compounds A, B, C, and D, a comparative compound, gefitinib, erlotinib, and afatinib.

Preferable examples of various definitions in the scope of the present invention used in this specification are explained below in detail.

In this specification, "EGFR" refers to a human epidermal growth factor receptor protein, and is also referred to as ErbB-1 or HER1.

In this specification, "wild-type EGFR" refers to EGFR free of somatic mutation, which is a protein comprising the amino acid sequence represented by SEQ ID NO: 1 (GenBank accession number: NP 005219.2).

In this specification, "exon 20 insertion mutation" refers to a mutation in which one or more amino acids (preferably 1 to 7, more preferably 1 to 4) are inserted in the exon 20 region (the 761st to 823rd amino acid sequence in SEQ ID NO: 1) of EGFR, and is preferably a mutation in which amino acid sequence FQEA (phenylalanine, glutamine, glutamic acid, and alanine in this order from the N-terminus) is inserted between the 763rd alanine and 764th tyrosine in the exon 20 region (A763_Y764insFQEA); a mutation in which amino acid sequence ASV (alanine, serine, and valine in this order from the N-terminus) is inserted between the 769th valine and 770th aspartic acid in the exon region (V769_D770insASV); a mutation in which amino acid sequence SVD (serine, valine, and aspartic acid in this order from the N-terminus) is inserted between the 770th aspartic acid and 771st asparagine in the exon 20 region (D770_N771insSVD); a mutation in which amino acid sequence NPG (asparagine, proline, and glycine in this order from the N-terminus) is inserted between the 770th aspartic acid and 771st asparagine in the exon 20 region (D770_N771insNPG); a mutation in which amino acid G (glycine) is inserted between the 770th aspartic acid and 771st asparagine (D770_N771insG); a mutation in which the 770th aspartic acid in the exon 20 region is deleted, and amino acid sequence GY (glycine and tyrosine in this order from the N-terminus) is inserted instead (D770>GY); a mutation in which amino acid N (asparagine) is inserted between the 771st asparagine and 772nd proline in the exon 20 region (N771_P772insN); a mutation in which amino acid sequence PR (proline and arginine in this order from the N-terminus) is inserted between the 772nd proline and 773rd histidine in the exon 20 region (P772_R773insPR); a mutation in which amino acid sequence NPH (asparagine, proline, and histidine in this order from the N-terminus) is inserted between the 773rd histidine and 774th valine in the exon 20 region (H773_V774insNPH); a mutation in which amino acid sequence PH (proline and histidine in this order from the N-terminus) is inserted between the 773rd histidine and 774th valine in the exon 20 region (H773_V774insPH); a mutation in which amino acid sequence AH (alanine and histidine in this order from the N-terminus) is inserted between the 773rd histidine and 774th valine in the exon 20 region (H773_V774insAH); a mutation in which amino acid H (histidine) is inserted between the 773rd histidine and 774th valine in the exon 20 region (H773_V774insH); a mutation in which amino acid sequence HV (histidine and valine in this order from the N-terminus) is inserted between the 774th valine and 775th cysteine in the exon 20 region (V774_C775insHV); a mutation in which amino acid sequence EAFQ (glutamic acid, alanine, phenylalanine, and glutamine in this order from the N-terminus) is inserted between the 761st alanine and 762nd glutamic acid in the exon 20 region (A761_E762insEAFQ); and the like. More preferable mutations include a mutation in which amino acid sequence ASV (alanine, serine, and valine in this order from the N-terminus) is inserted between the 769th valine and 770th aspartic acid in the exon 20 region (V769_D770insASV); a mutation in which amino acid sequence SVD (serine, valine, and aspartic acid in this order from the N-terminus) is inserted between the 770th aspartic acid and 771st asparagine in the exon 20 region (D770_N771insSVD); a mutation in which amino acid G (glycine) is inserted between the 770th aspartic acid and 771th asparagine in the exon 20 region (D770_N771insG); a mutation in which amino acid sequence NPH (asparagine, proline, and histidine in this order from the N-terminus) is inserted between the 773rd histidine and 774th valine in the exon 20 region (H773_V774insNPH); and a mutation in which amino acid sequence PH (proline and histidine in this order from the N-terminus) is inserted between the 773rd histidine and 774th valine in the exon 20 region (H773_V774insPH). More preferable mutations include a mutation in which amino acid sequence SVD (serine, valine, and aspartic acid in this order from the N-terminus) is inserted between the 770th aspartic acid and 771st asparagine in the exon 20 region (D770_N771insSVD); and a mutation in which amino acid G (glycine) is inserted between the 770th aspartic acid and 771st asparagine in the exon 20 region (D770_N771insG).

In this specification, the "malignant tumor patient expressing EGFR having exon 20 insertion mutation" refers to a malignant tumor patient expressing EGFR having exon 20 insertion mutation in at least one part of the exon 20 region of EGFR. The EGFR may have exon 20 insertion mutation in two or more different parts, but preferably one part thereof. Further, the EGFR may also have a mutation other than exon 20 insertion mutation (such as exon 19 deletion mutation, L858R mutation, or L790M mutation).

In the present invention, the method for detecting exon 20 insertion mutation of EGFR expressed in a malignant tumor patient is not particularly limited insofar as the method is capable of detecting the mutation, and any known detection methods may be used. The detection target in the detection of exon 20 insertion mutation may be any of genome sequence of EGFR gene, transcriptional product of EGFR gene, and EGFR protein.

The sample used in the detection of exon 20 insertion mutation is not particularly limited as long as the sample is a biological sample isolated from a malignant tumor patient, in particular, a sample that is obtained from a malignant tumor patient and contains malignant tumor cells. Examples of biological samples include body fluids (e.g., blood, urine, etc.), tissues, the extracts thereof, and the cultures of obtained tissues. The method for isolating a biological sample can be suitably selected depending on the type of biological sample.

The biological sample is prepared by being appropriately treated according to the detection method. Further, the reagent used for the detection (e.g., a reagent containing primer or probe) may be prepared by a conventional method according to the detection method.

In one embodiment of the present invention, the step for detecting the presence of exon 20 insertion mutation of EGFR expressed in a malignant tumor patient may be performed before the administration of antitumor agent to a malignant tumor patient.

Compounds A to D (Compounds A, B, C, and D) (in this specification, these compounds may also be generally referred to as a "compound of the present invention" or a "compound according to the present invention") and the production method thereof are explained below.

Compound A ((S)—N-(4-amino-6-methyl-5-(quinolin-3-yl)-8,9-dihydropyrimido[5,4-b]indolizin-8-yl)acrylamide) is represented by the following chemical formula.

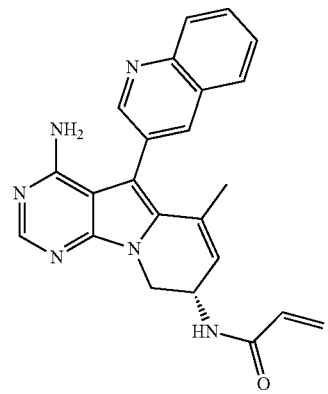 [SMILES: C=CC(=O)N[C@H]1C=C(C)c2c(-c3cnc4ccccc4c3)c3c(N)ncnc3n2C1]

Compound B ((S)—N-(4-amino-6-methylene-5-(quinolin-3-yl)-7,8-dihydro-6H-pyrimido[5,4-b]pyrrolizin-7-yl)acrylamide) is represented by the following chemical formula.

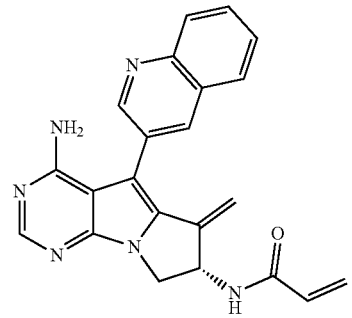 [SMILES: C=CC(=O)N[C@@H]1Cn2c(c(-c3cnc4ccccc4c3)c3c(N)ncnc32)C1=C]

Compound C ((S,E)—N-(4-amino-6-methylene-5-(quinolin-3-yl)-7,8-dihydro-6H-pyrimido[5,4-b]pyrrolizin-7-yl)-3-chloroacrylamide) is represented by the following chemical formula.

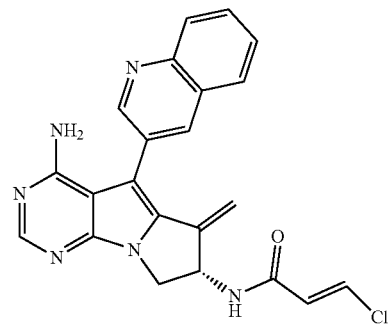 [SMILES: C=C1c2c(-c3cnc4ccccc4c3)c3c(N)ncnc3n2C[C@H]1NC(=O)/C=C/Cl]

Compound D ((R)—N-(4-amino-6-methyl-5-(quinolin-3-yl)-8,9-dihydropyrimido[5,4-b]indolizin-8-yl)-N-methylacrylamide) is represented by the following chemical formula.

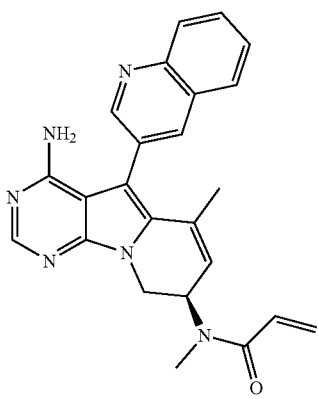 [SMILES: C=CC(=O)N(C)[C@@H]1C=C(C)c2c(-c3cnc4ccccc4c3)c3c(N)ncnc3n2C1]

Compounds A to D may be produced, for example, through the production method disclosed in WO2015/025936A1, the methods described in the Examples, and the like. However, the production methods of Compounds A to D are not limited to these reaction examples.

When Compounds A to D of the present invention have isomers such as optical isomers, stereoisomers, rotational isomers, and tautomers, any of the isomers and mixtures thereof are included within the scope of the compound of the present invention, unless otherwise specified. For example, when Compounds A to D of the present invention have optical isomers, racemic mixtures and the optical isomers separated from a racemic mixture are also included within the scope of the compound of the present invention, unless otherwise specified.

The salts of Compounds A to D refer to any pharmaceutically acceptable salts; examples include base addition salts and acid addition salts.

Examples of base addition salts include alkali metal salts such as sodium salts and potassium salts; alkaline earth metal salts such as calcium salts and magnesium salts; ammonium salts; and organic amine salts such as trimethylamine salts, triethylamine salts, dicyclohexylamine salts, ethanolamine salts, diethanolamine salts, triethanolamine salts, procaine salts, and N,N'-dibenzylethylenediamine salts.

Examples of acid addition salts include inorganic acid salts such as hydrochlorides, sulfates, nitrates, phosphates, and perchlorates; organic acid salts such as acetates, formates, maleates, fumarates, tartrates, citrates, ascorbates, and trifluoroacetates; and sulfonates such as methanesulfonates, isethionates, benzenesulfonates, and p-toluenesulfonates.

Compounds A to D and salts thereof also encompass prodrugs thereof. A prodrug refers to a compound that can be converted to Compounds A to D or a salt thereof through a reaction with an enzyme, gastric acid, or the like, under physiological conditions in vivo, i.e., a compound that can be converted to the compound of the present invention or a salt thereof by enzymatic oxidation, reduction, hydrolysis, or the like; or a compound that can be converted to Compounds A to D or a salt thereof by hydrolysis or the like with gastric acid or the like. Further, the prodrug may be compounds that can be converted to Compounds A to D or a salt thereof under physiological conditions, such as those described in "Iyakuhin no Kaihatsu [Development of Pharmaceuticals]," Vol. 7, Molecular Design, published in 1990 by Hirokawa Shoten Co., pp. 163-198.

Description of Diseases

Specific examples of tumors targeted in the present invention include, but are not particularly limited to, head and neck cancer, gastrointestinal cancer (esophageal cancer, stomach cancer, duodenal cancer, liver cancer, biliary cancer (e.g., gallbladder and bile duct cancer), pancreatic cancer, colorectal cancer (e.g., colon cancer, and rectal cancer), etc.), lung cancer (e.g., non-small-cell lung cancer, small-cell lung cancer, and mesothelioma), breast cancer, genital cancer (ovarian cancer, uterine cancer (e.g., cervical cancer, and endometrial cancer), etc.), urological cancer (e.g., kidney cancer, bladder cancer, prostate cancer, and testicular tumor), hematopoietic tumor (e.g., leukemia, malignant lymphoma, and multiple myeloma), osteosarcoma, soft-tissue sarcoma, skin cancer, brain tumor, and the like. Preferable examples include lung cancer, breast cancer, head and neck cancer, brain tumor, uterine cancer, hematopoietic tumor, or skin cancer.

When Compounds A to D or a salt thereof are used as a pharmaceutical agent, a pharmaceutical carrier can be added, if required, thereby forming a suitable dosage form according to prevention and treatment purposes. Examples of the dosage form include oral preparations, injections, suppositories, ointments, patches, and the like. Oral preparations are preferable. Such dosage forms can be formed by methods conventionally known to persons skilled in the art.

As the pharmaceutical carrier, various conventional organic or inorganic carrier materials used as preparation materials may be blended as an excipient, binder, disintegrant, lubricant, or colorant in solid preparations; or as a solvent, solubilizing agent, suspending agent, isotonizing agent, buffer, or soothing agent in liquid preparations. Moreover, pharmaceutical preparation additives, such as antiseptics, antioxidants, colorants, sweeteners, and stabilizers, may also be used, if required.

Oral solid preparations are prepared as follows. After an excipient is added optionally with a binder, disintegrant, lubricant, colorant, taste-masking or flavoring agent, etc., to Compounds A to D, the resulting mixture is formulated into tablets, coated tablets, granules, powders, capsules, or the like by ordinary methods.

Examples of excipients include lactose, sucrose, D-mannitol, glucose, starch, calcium carbonate, kaolin, microcrystalline cellulose, and silicic acid anhydride. Examples of binders include water, ethanol, 1-propanol, 2-propanol, simple syrup, liquid glucose, liquid α-starch, liquid gelatin, D-mannitol, carboxymethyl cellulose, hydroxypropyl cellulose, hydroxypropyl starch, methyl cellulose, ethyl cellulose, shellac, calcium phosphate, polyvinylpyrrolidone, and the like. Examples of disintegrators include dry starch, sodium alginate, powdered agar, sodium hydrogen carbonate, calcium carbonate, sodium lauryl sulfate, stearic acid monoglyceride, lactose, and the like. Examples of lubricants include purified talc, sodium stearate, magnesium stearate, borax, polyethylene glycol, and the like. Examples of colorants include titanium oxide, iron oxide, and the like. Examples of taste-masking or flavoring agents include sucrose, bitter orange peel, citric acid, tartaric acid, and the like.

When a liquid preparation for oral administration is prepared, a taste-masking agent, a buffer, a stabilizer, a flavoring agent, and the like may be added to Compounds A to D; and the resulting mixture may be formulated into an oral liquid preparation, syrup, elixir, etc., according to an ordinary method.

Examples of taste-masking or flavoring agents include those mentioned above. Examples of buffer agents include sodium citrate and the like. Examples of stabilizers include tragacanth, gum arabic, gelatin, and the like. As necessary, these preparations for oral administration may be coated according to methods known in the art with an enteric coating or other coating for the purpose of, for example, persistence of effects. Examples of such coating agents include hydroxypropyl methylcellulose, ethyl cellulose, hydroxymethyl cellulose, hydroxypropyl cellulose, polyoxyethylene glycol, and Tween 80 (registered trademark).

When an injection agent is prepared, a pH regulator, a buffer, a stabilizer, an isotonizing agent, a local anesthetic, and the like, may be added to Compounds A to D; and the mixture may be formulated into a subcutaneous, intramuscular, or intravenous injection according to an ordinary method.

Examples of the pH adjuster and the buffer used herein include sodium citrate, sodium acetate, and sodium phosphate. Examples of the stabilizer include sodium pyrosulfite, EDTA, thioglycolic acid, and thiolactic acid. Examples of the local anesthetic include procaine hydrochloride and lidocaine hydrochloride. Examples of the tonicity agent include sodium chloride, glucose, D-mannitol, and glycerol.

When a suppository is prepared, pharmaceutically acceptable carriers known by a person skilled in the art, such as polyethylene glycol, lanolin, cacao butter, and fatty acid triglyceride; and as necessary, surfactants such as Tween 80 (registered trademark), may be added to Compounds A to D, and the resulting mixture may be formulated into a suppository according to an ordinary method.

When an ointment is prepared, a commonly used base, stabilizer, wetting agent, preservative, and the like, may be blended into Compounds A to D, as necessary; and the obtained mixture may be mixed and formulated into an ointment according to an ordinary method.

Examples of the base include liquid paraffin, white petrolatum, white beeswax, octyl dodecyl alcohol, and paraffin.

Examples of the preservative include methyl paraoxybenzoate, ethyl paraoxybenzoate, and propyl paraoxybenzoate.

When a patch is prepared, the above-described ointment, cream, gel, paste, or the like, may be applied to an ordinary substrate according to an ordinary method.

Examples of substrates include woven fabrics or nonwoven fabrics comprising cotton, staple fibers, or chemical fibers; and films or foam sheets of soft vinyl chloride, polyethylene, polyurethane, etc., are suitable.

The amount of Compounds A to D to be incorporated in each of such dosage unit forms depends on the condition of the patient to whom the compound is administered, the dosage form thereof, etc. In general, in the case of an oral agent, the amount of the compound is preferably 0.05 to 1000 mg per dosage unit form. In the case of an injection, the amount of the compound is preferably 0.01 to 500 mg per dosage unit form; and in the case of a suppository, the amount of the compound is preferably 1 to 1000 mg per dosage unit form.

Further, the daily dose of the medicine in such a dosage form depends on the condition, body weight, age, sex, etc., of the patient, and cannot be generalized. For example, the daily dose for an adult (body weight: 50 kg) of Compounds A to D as an active ingredient may be generally 0.05 to 5000 mg, and preferably 0.1 to 1000 mg; and is preferably administered in one dose, or in two to three divided doses, per day.

The present invention also provides a method for treating a malignant tumor patient, comprising the step of administering an effective amount of an antitumor agent comprising a compound selected from the group consisting of Compounds A to D or a salt thereof to a malignant tumor patient expressing EGFR having exon 20 insertion mutation.

The present invention also provides a compound selected from the group consisting of Compounds A to D, or a salt thereof for treating a malignant tumor patient expressing EGFR having exon 20 insertion mutation.

The present invention also provides use of a compound selected from the group consisting of Compounds A to D or a salt thereof for treating a malignant tumor patient expressing EGFR having exon 20 insertion mutation.

The present invention also provides use of a compound selected from the group consisting of Compounds A to D or a salt thereof for the production of an antitumor agent for treating a malignant tumor patient expressing EGFR having exon 20 insertion mutation.

The present invention is also a method for predicting therapeutic effects of chemotherapy using an antitumor agent comprising, as an active ingredient, a compound selected from the group consisting of Compounds A to D or a salt thereof in a malignant tumor patient, the method comprising steps (1) and (2) below:

(1) a step of detecting the presence or absence of mutation of EGFR gene contained in a biological sample obtained from the patient; and (2) a step of predicting that the chemotherapy is highly likely to exhibit sufficient therapeutic effects with respect to the patient when the results of the detection in step (1) found that the EGFR gene has exon 20 insertion mutation.

The present invention is also a method for treating a malignant tumor patient, the method comprising steps (1) to (3) below:

(1) a step of detecting the presence or absence of mutation of EGFR gene contained in a biological sample obtained from the patient;

(2) a step of predicting that the chemotherapy using an antitumor agent comprising a compound selected from the group consisting of Compounds A to D or a salt thereof is highly likely to exhibit sufficient therapeutic effects with respect to the patient when the results of the detection in step (1) found that the EGFR gene has exon 20 insertion mutation; and (3) a step of administering the antitumor agent to a patient who was predicted highly likely to sufficiently respond to the chemotherapy in step (2).

The base sequence of EGFR gene is publicly known. The GenBank accession number of the base sequence of cDNA is NM_005228.4.

The "therapeutic effects" can be evaluated by tumor shrinkage effects, relapse-suppressing effects, life-prolonging effects, and the like. The relapse-suppressing effects may be shown as degree of the extension of non-relapse period and/or the degree of the improvement in relapse rate; and the life-prolonging effects may be shown as the degree of the entire survival time and/or the degree of the extension of the median of progression-free survival, or the like. The "sufficient therapeutic effects" of the chemotherapy using an antitumor agent comprising, as an active ingredient, Compound A or a salt thereof means that superior therapeutic effects are obtained by the administration of the antitumor agent comprising, as an active ingredient, Compound A or a salt thereof, such as significant extension of survival time, significant suppression of relapse, and the like, compared with non-administration.

EXAMPLES

The following describes the present invention in more detail with reference to the following Test Examples. However, the present invention is not limited to these Examples (Test Examples).

Test Example 1

In Vitro Drug Efficacy Test
Evaluation of Cell Growth Inhibitory Effect on Wild-Type EGFR- or Mutant EGFR-Expressing Cell Lines (1)

The inhibitory activity of compounds against wild-type EGFR and mutant EGFR was evaluated using Ba/F3 cells (mouse B-lymphocyte precursor cell lines) to which human EGFR genes were introduced. The Ba/F3 cells were maintained in an RPMI-1640 medium (Thermo Fisher Scientific) containing 10% fetal bovine serum (FBS), 100 U/mL penicillin/100m/mL streptomycin (Thermo Fisher Scientific), and 1 ng/mL mouse interleukin-3 (mIL-3) (CST). A PB-CMV-MCS-EF1-GFP+Puro vector or PB-CMV-MCS-EF1-RFP+Puro vector into which a human EGFR gene (wild-type (WT), V769_D770insASV (insASV), D770_N771insSVD (insSVD), D770_N771insG (insG), H773_V774insNPH (insNPH), or H773_V774insPH (insPH)) was encoded was introduced to the cells, together with a Super PiggyBac transposase expression vector, by electroporation using an Amaxa (trademark) Cell Line Nucleofector (trademark) Kit V, followed by selection using puromycin (SIGMA). Ba/F3 cells expressing wild-type EGFR (which hereinafter also referred to as "Ba/F3-EGFR_WT") exhibited mIL-3-independent growth in the presence of 50 ng/mL EGF (R&D Systems); and Ba/F3 cells expressing EGFR exon 20 insertion mutation (which hereinafter also referred to as "Ba/F3-EGFRinsASV," "Ba/F3-EGFRinsSVD," "Ba/F3-EGFRinsG," "Ba/F3-EGFRinsNPH," or "Ba/F3-EGFRinsPH") exhibited mIL-3-independent growth in the absence of EGF.

To evaluate the cell growth inhibitory effect, Ba/F3-EGFR_WT cells were suspended in an RPMI-1640 medium containing 10% FBS, 100 U/mL penicillin, 100m/mL streptomycin, and 50 ng/mL EGF; and the cell suspension was seeded in each well of a 96-well flat-bottom microplate such that the cell count per well was 30,000. The Ba/F3 cells expressing EGFR exon 20 insertion mutation were suspended in an RPMI-1640 medium containing 10% FBS, 100 U/mL penicillin, and 100 µg/mL streptomycin; and the cell suspension was seeded in each well of a 96-well flat-bottom microplate such that the cell count per well was 15,000. Subsequently, (S)—N-(4-amino-6-methyl-5-(quinolin-3-yl)-8,9-dihydropyrimido[5,4-b]indolizin-8-yl)acrylamide (compound A), (S)—N-(4-amino-6-methylene-5-(quinolin-3-yl)-7,8-dihydro-6H-pyrimido[5,4-b]pyrrolizin-7-yl)acrylamide (compound B), (S,E)—N-(4-amino-6-methylene-5-(quinolin-3-yl)-7,8-dihydro-6H-pyrimido[5,4-b]pyrrolizin-7-yl)-3-chloroacrylamide (compound C), and (R)—N-(4-amino-6-methyl-5-(quinolin-3-yl)-8,9-dihydropyrimido [5,4-b]indolizin-8-yl)-N-methylacrylamide (compound D) prepared in accordance with the production method disclosed in PTL 2, and (S)—N-(4-amino-5-(quinolin-3-yl)-6,7,8,9-tetrahydropyrimido[5,4-b]indolizin-8-yl)acrylamide prepared in accordance with the production method disclosed in WO2013/125709A1 (the compound of Example 1 in WO2013/125709A1, which hereinafter also referred to as "comparative compound") were dissolved in DMSO, and diluted with DMSO or the medium used for suspending the cells. These compounds were individually added to each well of the culture plate of the cells, and incubated in a 5% $CO_2$ gas-containing incubator at 37° C. for 3 days. The cell count after incubation was measured using a CellTiter-Glo (trademark) Luminescent Cell Viability Assay (Promega Corporation) in accordance with the manufacturer's recommended protocol. The growth rate was calculated using the following formula, and the concentration of each test compound for 50% inhibition ($IC_{50}$ (µM)) was determined.

$$\text{Growth Rate (\%)} = T/C \times 100$$

T: the luminescence intensity of a well to which a test compound was added.
C: the luminescence intensity of a well to which the test compound was not added.

Additionally, the ratio of $IC_{50}$ between wild-type EGFR and EGFR exon 20 insertion mutation was determined using the following formula. FIG. 1 illustrates the results.

$IC_{50}$ Ratio=$IC_{50}$ (WT)/$IC_{50}$ (ex20ins)
$IC_{50}$ (WT): $IC_{50}$ for wild-type EGFR
$IC_{50}$ (ex20ins): $IC_{50}$ for EGFR exon 20 insertion mutation As is clear from FIG. 1, compounds A to D exhibited a cell growth inhibitory effect on cell lines expressing EGFR exon 20 insertion mutations; and their mutation selectivity was higher than that of the comparative compound, gefitinib, erlotinib, and afatinib.

Test Example 2

Cell Growth Inhibitory Effect on Wild-Type EGFR- or Mutant EGFR-Expressing Human Cell Lines (2)

To evaluate the inhibitory activity of compounds against wild-type EGFR and mutant EGFR, the following cells were used: NCI-H1975 cells, which are human pulmonary adenocarcinoma cell lines expressing EGFR with mutation D770_N771insSVD by gene modification (which hereinafter also referred to as "H1975-EGFRinsSVD"); and A431 cells, which are human epithelial cancer cell lines expressing wild-type EGFR. H1975-EGFRinsSVD cells were prepared as follows. A PB-CMV-MCS-EF1-RFP+Puro vector into which D770_N771insSVD (insSVD) was encoded was introduced into NCI-H1975 cells, together with a Super PiggyBac Transposase expression vector, by electroporation using an Amaxa (trademark) Cell Line Nucleofector (trademark) Kit R, followed by selection using puromycin (SIGMA). XTN (trademark) TALENs Site-Specific Nucleases (Transposagen) were introduced into the cells by electroporation using the Amaxa (trademark) Cell Line Nucleofector (trademark) Kit R, and endogenous-EGFR (T790M/L858R)-knockout cells were selected by sequencing.

To evaluate the cell growth inhibitory effect, individual types of cells were suspended in a medium recommended by ATCC. The cell suspensions were seeded in each well of respective 96-well flat-bottom plates such that the cell count per well was 3,000, and incubated in a 5% $CO_2$-containing incubator at 37° C. for 1 day. Compound A, the comparative compound, gefitinib, erlotinib, and afatinib were individually dissolved in DMSO, and diluted with DMSO such that these test compounds have a concentration 200 times higher than the final concentration. These DMSO solutions of the test compounds were diluted with the medium used for suspending the cells, and added to each well of the culture plates of the cells such that DMSO has a final concentration of 0.5%, and the cells were incubated in a 5% $CO_2$- containing incubator at 37° C. for 3 days. The cell count at the time incubation started (day 0) and the cell count after incubation (day 3) were measured using a CellTiter-Glo (trademark) Luminescent Cell Viability Assay (Promega Corporation) in accordance with the manufacturer's recommended protocol. The growth rate was calculated using the following formula, and the concentration of each test compound for 50% inhibition ($GI_{50}$ (μM)) was determined. Table 1 illustrates the results.

1) If T on day 3≥C on day 0:

Growth Rate (%)=(T on day 3−C on day 0)/(C on day 3−C on day 0)×100

T: the luminescence intensity of a well to which a test compound was added.
C: the luminescence intensity of a well to which the test compound was not added.
Day 0: the day on which a test compound was added.
Day 3: the day on which evaluation was performed.

2) If T on day 3<C on day 0:

Growth Rate (%)=(T on day 3−C on day 0)/(C on day 0)×100

T: the luminescence intensity of a well to which a test compound was added.
C: the luminescence intensity of a well to which the test compound was not added.
Day 0: the day on which a test compound was added.
Day 3: the day on which evaluation was performed.

TABLE 1

| | $GI_{50}$ (μM) | |
| --- | --- | --- |
| | A431 | H1975 EGFRinsSVD |
| Compound A | 0.396 | 0.031 |
| Comparative Compound | 0.543 | 0.364 |
| Gefitinib | 0.310 | 1.903 |
| Erlotinib | 0.612 | 2.775 |
| Afatinib | 0.023 | 0.189 |
| Osimertinib | 0.321 | 0.194 |

Figure 2:
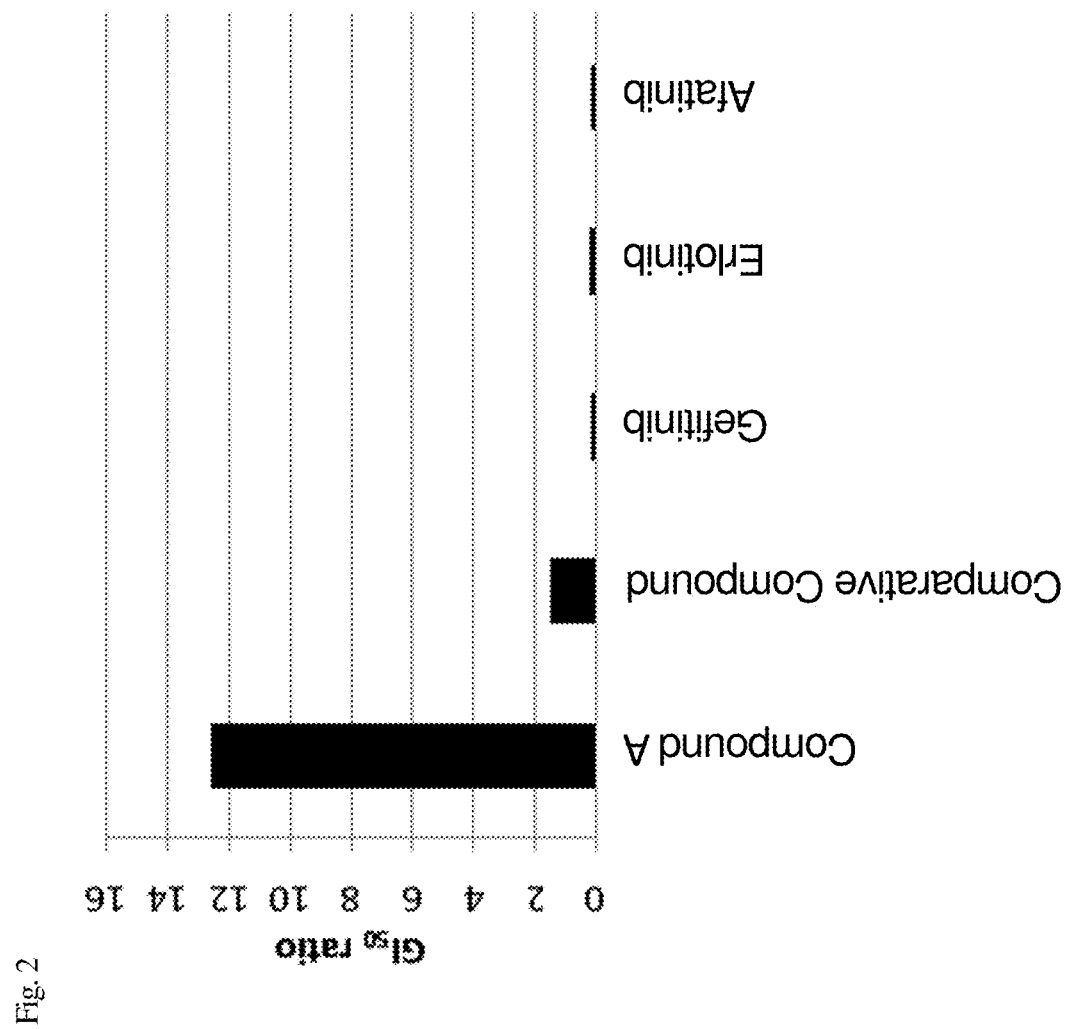
FIG. 2 illustrates $GI_{50}$ ratios of wild-type EGFR to EGFR exon 20 insertion mutations calculated from the results of a test for cell growth inhibition on wild-type EGFR-expressing human cell lines and mutant EGFR-expressing human cell lines by compound A, a comparative compound, gefitinib, erlotinib, and afatinib.
Figure 3:
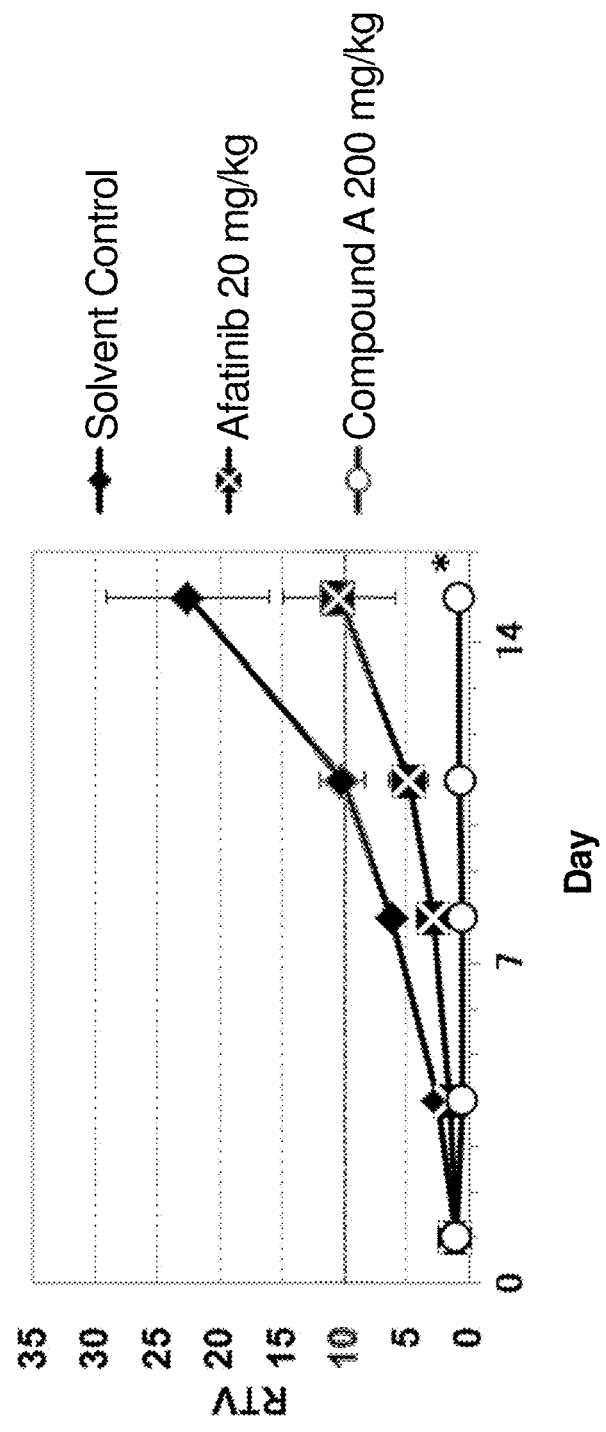
FIG. 3 illustrates the relative tumor volume (which hereinafter also referred to as "RTV") of mouse models that were subcutaneously transplanted with mutant EGFR-expressing cell lines (NIH3T3-EGFRinsASV cells) to measure the antitumor effect of compound A.
Figure 4:
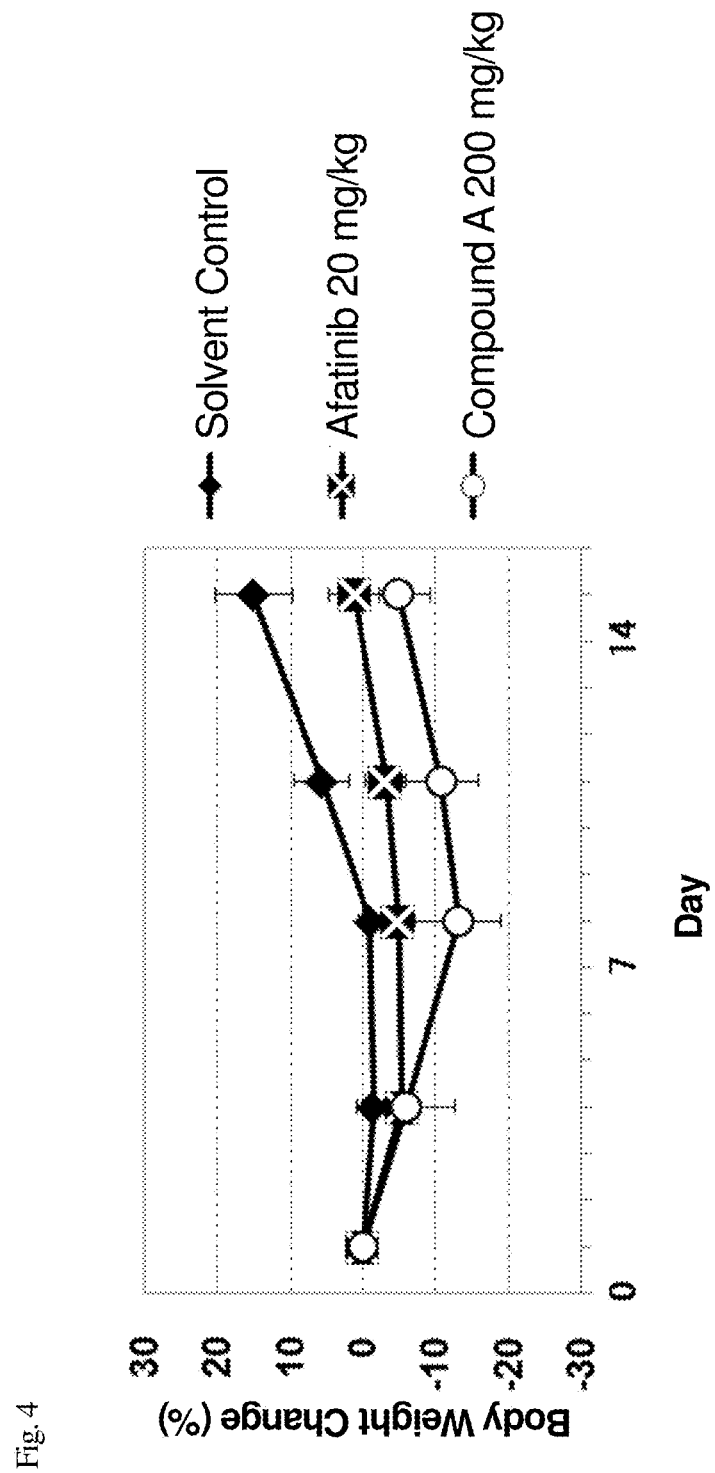
FIG. 4 illustrates the body weight change after grouping of mouse models that were subcutaneously transplanted with mutant EGFR-expressing cell lines (NIH3T3-EGFRinsASV cells) to measure the toxicity of compound A.
Figure 5:
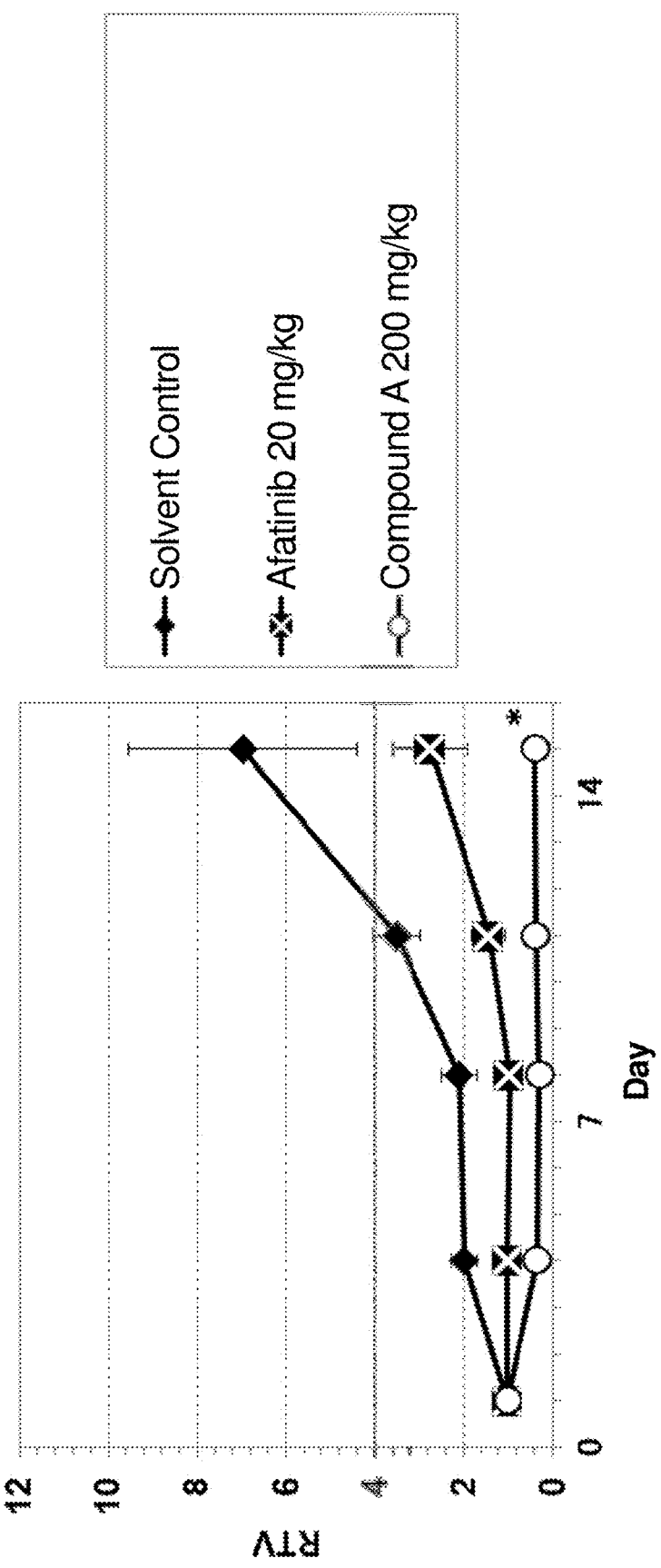
FIG. 5 illustrates the relative tumor volume of mouse models that were subcutaneously transplanted with mutant EGFR-expressing cell lines (NIH3T3-EGFRinsSVD cells) to measure the antitumor effect of compound A.
Figure 6:
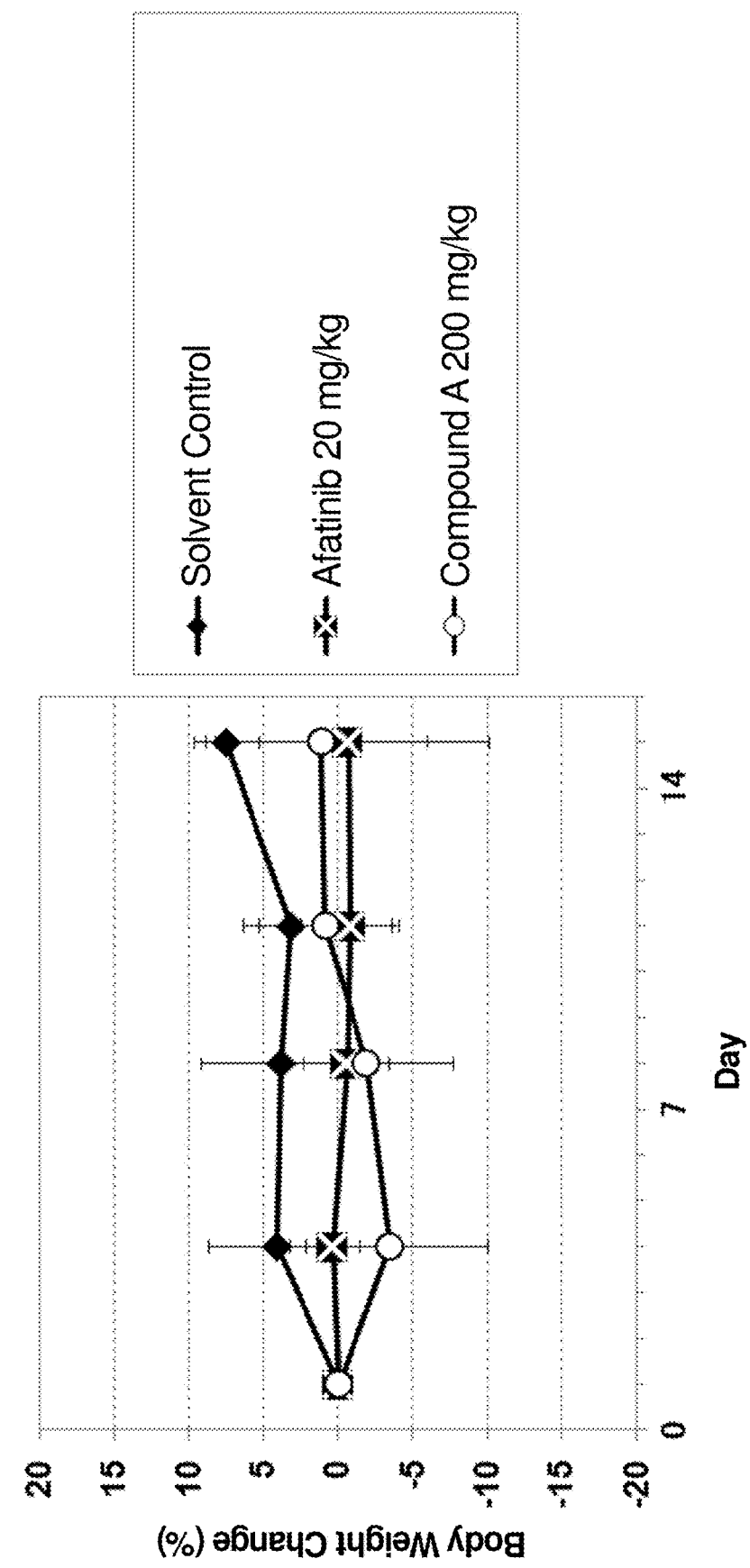
FIG. 6 illustrates the body weight after grouping of mouse models that were subcutaneously transplanted with mutant EGFR-expressing cell lines (NIH3T3-EGFRinsSVD cells) to measure the toxicity of compound A.
Figure 7:
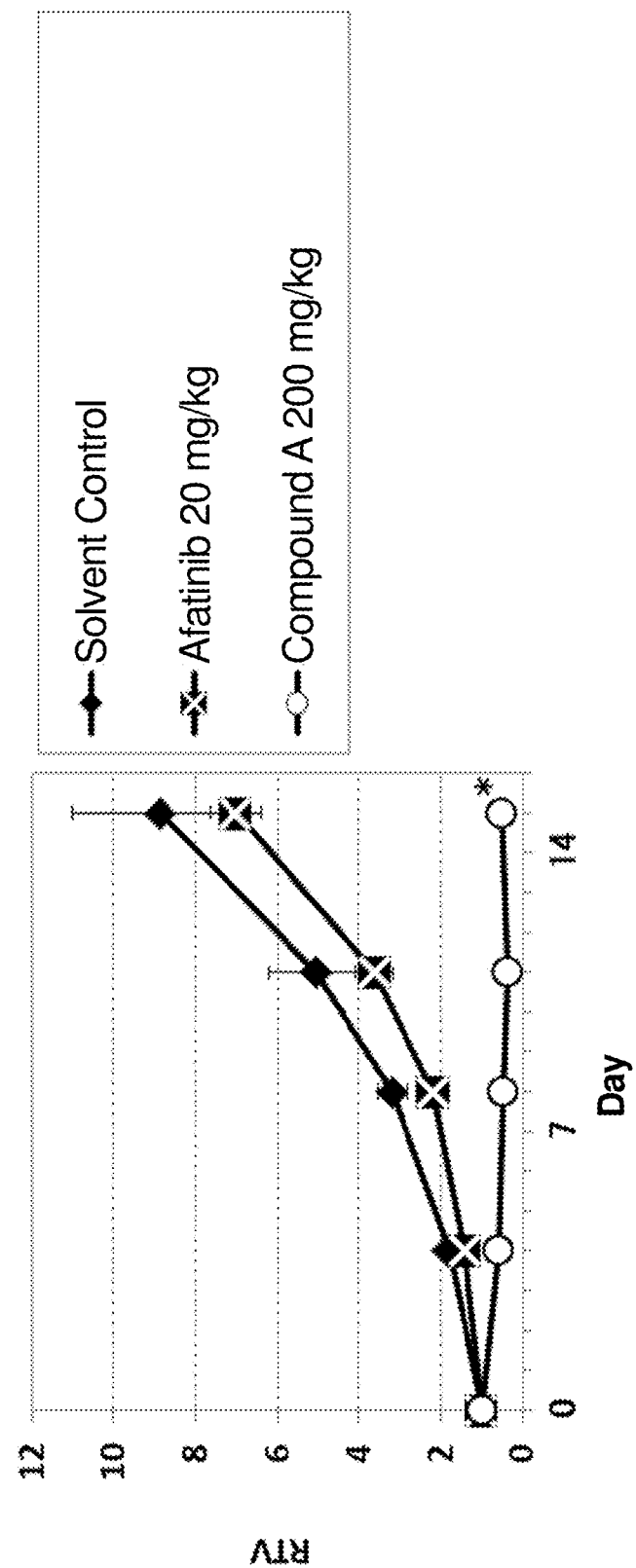
FIG. 7 illustrates the relative tumor volume of mouse models that were subcutaneously transplanted with mutant EGFR-expressing cell lines (H1975-EGFRinsSVD cells) to measure the antitumor effect of compound A.
Figure 8:
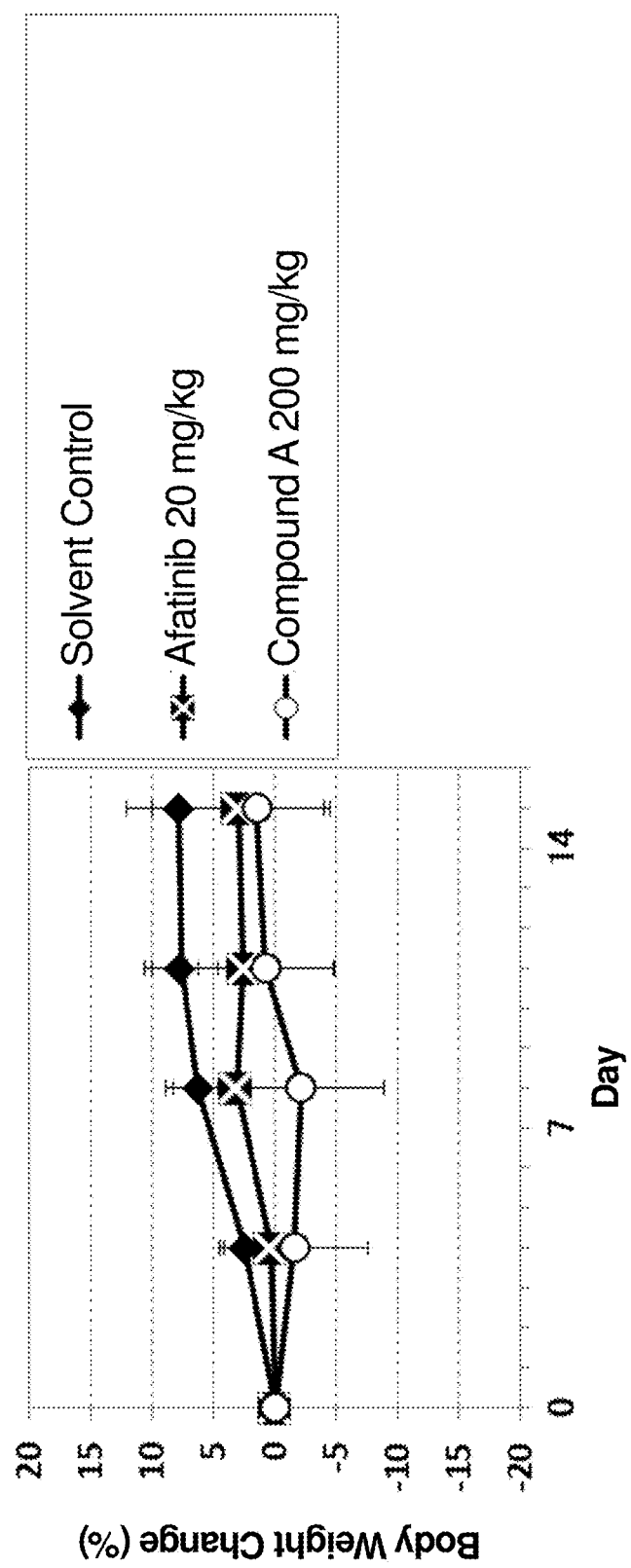
FIG. 8 illustrates the body weight after grouping of mouse models that were subcutaneously transplanted with mutant EGFR-expressing cell lines (H1975-EGFRinsSVD cells) to measure the toxicity of compound A.

Additionally, the ratio of $GI_{50}$ between wild-type EGFR and EGFR exon 20 insertion mutation was determined using the following formula. Table 2 illustrates the results.
$GI_{50}$ Ratio=$GI_{50}$ (A431)/$GI_{50}$ (H1975 EGFRinsSVD)
$GI_{50}$ (A431): $GI_{50}$ for wild-type EGFR
$GI_{50}$ (H1975 EGFRinsSVD): $GI_{50}$ for EGFR exon 20 insertion mutation As is clear from Table 1 and FIG. 2, compound A exhibited an cell growth inhibitory effect on cell lines expressing EGFR exon 20 insertion mutation, and its mutation selectivity was higher than that of the comparative compound, gefitinib, erlotinib, afatinib, and osimertinib.

Test Example 3

Evaluation of Phosphorylated EGFR Inhibitory Activity Against Wild-Type EGFR- or Mutant EGFR-Expressing Cell Lines (1)

A431 cells, which are human epithelial cancer cell lines overexpressing wild-type EGFR and H1975-EGFRinsSVD cells, which are human pulmonary adenocarcinoma cell lines expressing EGFR with mutation D770_N771insSVD by gene modification, were suspended in respective mediums. These cell suspensions were individually seeded into a 60-mm dish, and incubated in a 5% $CO_2$-containing incubator at 37° C. for 1 day. Compound A was dissolved in DMSO, and diluted with DMSO such that the test compound has a concentration 1000 times higher than the final concentration. The DMSO solution of the test compound was diluted with each medium used for suspending the cells, and each diluted solution was added to respective culture dishes of the cells such that DMS 0 has a final concentration of 0.1%, followed by incubation in a 5% $CO_2$-containing incubator at 37° C. for 6 hours. After incubation, the cells were collected, and stored at −80° C. in the form of pellets until use. A RIPA buffer (Thermo Fisher Scientific) containing a protease inhibitor cocktail (Thermo Fisher Scientific) was added to the pellets, and proteins within the cells were extracted. The concentration of the proteins were measured using a BCA protein assay kit (Thermo Fisher Scientific), and each sample was adjusted so as to have a protein concentration suitable for measurement of phosphorylated EGFR expression. The phosphorylated EGFR expression was measured using a Simple Western (trademark) assay system (ProteinSimple) in accordance with the manufacturer's recommended protocol. The primary antibody used in measurement was a Phospho-EGF Receptor (Tyr1068) #3777 (CST) diluted to 1/50.

For each type of cells, a calibration curve of the protein concentration (x axis) and the phosphorylated EGFR expression level (y axis) was prepared, and the phosphorylated EGFR expression level of each sample was converted to a protein concentration based on the calibration curve. The phosphorylated EGFR rate was calculated using the following formula to determine the concentration of the test compound at which phosphorylated EGFR was inhibited by 50% ($IC_{50}$ (μM)).

Phosphorylated EGFR Rate (%)=T/C×100

T: an equivalent amount for the protein concentration of a sample to which the test compound was added.
C: an equivalent amount for the protein concentration of a sample to which the test compound was not added.

Additionally, the selectivity for wild-type EGFR and EGFR exon 20 insertion mutation was calculated using the following formula. Table 2 illustrates the results.
$IC_{50}$Ratio=$IC_{50}$ (A431)/$IC_{50}$ (H1975 EGFRinsSVD)
$IC_{50}$ (A431): $IC_{50}$ for wild-type EGFR
$IC_{50}$ (H1975 EGFRinsSVD): $IC_{50}$ for EGFR exon 20 insertion mutation

TABLE 2

| | $IC_{50}$ (μM) | |
| --- | --- | --- |
| | A431 | H1975 EGFRinsSVD |
| $IC_{50}$ (μM) | 0.535 | 0.023 |
| $IC_{50}$ Ratio | — | 23.3 |

As is clear from Table 2, compound A exhibited a selective inhibition activity against EGFR exon 20 insertion mutation.

Test Example 4

Evaluation of Phosphorylated EGFR Inhibitory Activity Against Wild-Type EGFR- or Mutant EGFR-Expressing Cell Lines (2)

The autophosphorylation inhibitory activity of a compound against wild-type EGFR and mutant EGFR was evaluated using NIH-3T3 cells, which are mouse fibroblast cell lines to which human EGFR gene was introduced.

NIH-3T3 cells were maintained in a D-MEM (high-glucose) medium (Wako Pure Chemical Industries, Ltd.) containing 10% newborn calf serum (NBCS), 1,500 mg/L sodium hydrogen carbonate, and 100 U/mL penicillin/100m/mL streptomycin (Thermo Fisher Scientific). A PB-CMV-MCS-EF1-RFP+Puro vector into which a human EGFR gene (WT, insASV, insSVD, insG, insNPH, or insPH) was encoded was introduced into the cells, together with a Super PiggyBac Transposase expression vector, by electroporation using an Amaxa (trademark) Cell Line Nucleofector (trademark) Kit R, followed by selection using puromycin (SIGMA). NIH-3T3 cells expressing wild-type EGFR (which hereinafter also referred to as "NIH3T3-EGFR_WT") exhibited growth in the presence of 50 ng/mL EGF (R&D Systems) under 1% NBCS conditions. NIH-3T3 cells expressing EGFR exon 20 insertion mutation (which hereinafter also referred to as "NIH3T3-EGFRinsASV," "NIH3T3-EGFRinsSVD," "NIH3T3-EGFRinsG," "NIH3T3-EGFRinsNPH," or "NIH3T3-EGFRinsPH") exhibited growth in the absence of EGF under 1% NBCS conditions.

To evaluate EGFR-autophosphorylation inhibitory activity, NIH3T3 cells to which human EGFR was introduced were suspended in respective mediums. These cell suspensions were individually seeded into a 60-mm dish or 6-well flat-bottom plate, and incubated in a 5% $CO_2$-containing incubator at 37° C. for 1 day. Compound A was dissolved in DMSO, and diluted with DMSO such that the test compound has a concentration 400 times higher than the final concentration. The DMSO solutions of the test compound were diluted with the medium used for suspending the cells, and added to the culture dishes of the cells such that DMSO has a final concentration of 0.25%. Further, EGF was added to the culture dish of NIH3T3-EGFR_WT cells to give a final concentration of 50 ng/mL. The culture dishes were all subjected to incubation in a 5% $CO_2$-containing incubator at 37° C. for 6 hours. After incubation, the cells were collected, and stored at −80° C. in the form of pellets until use. A RIPA buffer (Thermo Fisher Scientific) containing a protease inhibitor cocktail (Thermo Fisher Scientific) was added to the pellets, and proteins within the cells were extracted. The protein concentration was measured using a BCA protein assay kit (Thermo Fisher Scientific), and each sample was adjusted to a protein concentration suitable for measurement of phosphorylated EGFR expression. The phosphorylated EGFR expression was measured using a Simple Western (trademark) assay system (ProteinSimple) in accordance with the manufacturer's recommended protocol. The primary antibody used in measurement was a Phospho-EGF Receptor (Tyr1068) #3777 (CST) diluted to 1/50.

For each type of cells, a calibration curve of the protein concentration (x axis) and the phosphorylated EGFR expression level (y axis) was prepared, and the phosphorylated EGFR expression level of each sample was converted to a protein concentration based on the calibration curve. The phosphorylated EGFR inhibitory rate was calculated using the following formula to determine the concentration of the test compound at which phosphorylated EGFR was inhibited by 50% ($IC_{50}$ (μM)).

Phosphorylated EGFR Inhibitory Rate (%)=*T*/*C*×100

T: an equivalent amount for the protein concentration of a sample to which the test compound was added.
C: an equivalent amount for the protein concentration of a sample to which the test compound was not added.

Additionally, the selectivity for wild-type EGFR and EGFR exon 20 insertion mutation was calculated using the following formula. Table 3 illustrates the results.

$IC_{50}$ Ratio=$IC_{50}$ (WT)/$IC_{50}$ (EGFR exon 20 insertion mutation)

TABLE 3

|  | WT | insASV | insSVD | insG | insNPH | insPH |
|---|---|---|---|---|---|---|
| $IC_{50}$ (μM) | 0.571 | 0.197 | 0.033 | 0.073 | 0.083 | 0.159 |
| $IC_{50}$ Ratio | — | 2.9 | 17.1 | 7.9 | 6.9 | 3.6 |

As is clear from Table 3, compound A exhibited a selective inhibition activity against various EGFR exon 20 insertion mutations.

As is clear from the results of Test Examples 1 to 4, compounds A to D exhibited a cell growth inhibitory effect, accompanied by an EGFR inhibitory effect, on cell lines expressing EGFR exon 20 insertion mutation; and the effect and mutation selectivity were higher than those of the comparative compound, gefitinib, erlotinib, afatinib, and osimertinib.

Test Example 5

In Vivo Drug Efficacy Test
Evaluation of Antitumor Effect on Model Subcutaneously Transplanted with Mutant EGFR-Expressing Cell Lines Nude mice were subcutaneously transplanted with NIH3T3-EGFRinsASV cells, NIH3T3-EGFRinsSVD cells, or H1975-EGFRinsSVD cells to which human mutant EGFR was introduced. At the point at which the tumor volume of the tumor engrafted in the nude mice grew to about 100 to 200 mm³, the mice were allocated into groups, 5 to 6 mice for each group, by stratified randomization such that the average tumor volume between the groups was uniform. The mice were then orally administered compound A or afatinib once daily for 14 consecutive days.

The dose of afatinib was 20 mg/kg/day, which is the maximum tolerated dose (the highest dose at which the weight loss during a dosing period is less than 20%) for 14 days, a dosing period of this test; and the dose of compound A was 200 mg/kg/day (maximum tolerated dose). The maximum tolerated dose was determined in accordance with the "Guidelines Involving Experimental Neoplasia Proposals in Mice and Rats" of the National Cancer Institute (NCI), from a humanitarian perspective.

To compare the changes in growth of tumor over time due to administration of the individual test compounds, a relative tumor volume (which hereinafter also referred to as "RTV") was calculated based on the tumor volume at the time the mice were divided into groups (which is taken as 1 for the tumor growth ratio), using the following formula. For a toxicity index, the body weight was measured over time, and the average body weight change (which hereinafter also referred to as "BWC (%)") from the day on which the mice were divided into groups was calculated in accordance with the following formula. FIGS. 3 to 8 illustrate changes in the average RTV and the average BWC of the mice.
RTV=(the tumor volume on the day a tumor volume was measured)/(the tumor volume on the day mice were divided into groups)
BWC (%)=(the body weight measured on body weight measurement day)/(the body weight on the day mice were divided into groups)

When the average RTV of the group administered with compound A on the final evaluation day was smaller than the average RTV of the group administered with afatinib, while also exhibiting a statistically significant difference (Student's t-test, p<0.05), compound A was determined to be significantly more effective than afatinib. Such a case is indicated by the symbol "*" in the figures. The T/C (%) on the final evaluation day was calculated in accordance with the following formula. Table 4 illustrates the results.

TABLE 4

| Transplanted Tumor | Compound | 20 mg/kg | 200 mg/kg |
|---|---|---|---|
| NIH3T3 EGFRinsASV | Compound A of the Present Invention | N.D. | 3 |
| | Afatinib | 46 | N.D. |
| NIH3T3 EGFRinsSVD | Compound A of the Present Invention | N.D. | 5 |
| | Afatinib | 39 | N.D. |
| H1975 EGFRinsSVD | Compound A of the Present Invention | N.D. | 6 |
| | Afatinib | 79 | N.D. |

N.D.: No data are available.

As is clear from the results of FIGS. 3 to 8 and Table 4, compound A exhibited a remarkable antitumor effect on cell lines expressing EGFR exon 20 insertion mutation subcutaneously transplanted into nude mice. The effect was also higher than that of afatinib, without symptoms such as serious weight loss, abnormal feces, or abnormal skin in mice.

Test Example 6

In Vivo Drug Efficacy Test
Evaluation of Antitumor Effect on Model Subcutaneously Transplanted with Mutant EGFR-Expressing Cell Lines Nude mice were subcutaneously transplanted with NIH3T3-EGFRinsNPH cells into which human mutant EGFR was introduced. At the point at which the tumor volume of the tumor engrafted in the nude mice grew to about 100 to 200 mm$^3$, the mice were allocated into groups, 6 mice for each group, by stratified randomization such that the average tumor volume between the groups was uniform. The mice were then orally administered compound A or afatinib once daily for 10 consecutive days.

The dose of afatinib was 20 mg/kg/day, which is the maximum tolerated dose (the highest dose at which the weight loss during a dosing period is less than 20%); and the dose of compound A was 100, and 200 mg/kg/day. The maximum tolerated dose was determined in accordance with the "Guidelines Involving Experimental Neoplasia Proposals in Mice and Rats" of the National Cancer Institute (NCI), from a humanitarian perspective.

Figure 9:
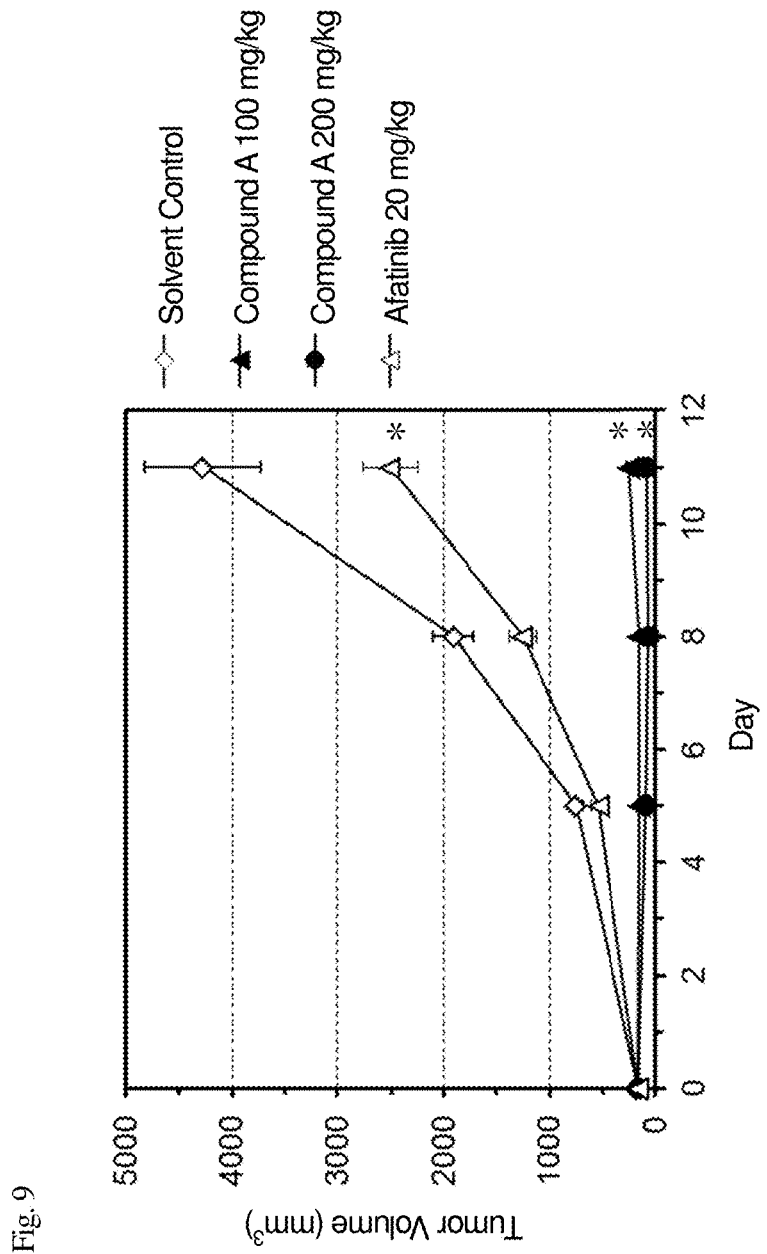
FIG. 9 illustrates the tumor volume of mouse models that were subcutaneously transplanted with mutant EGFR-expressing cell lines (NIH3T3-EGFRinsNPH) to measure the antitumor effect of compound A.
Figure 10:
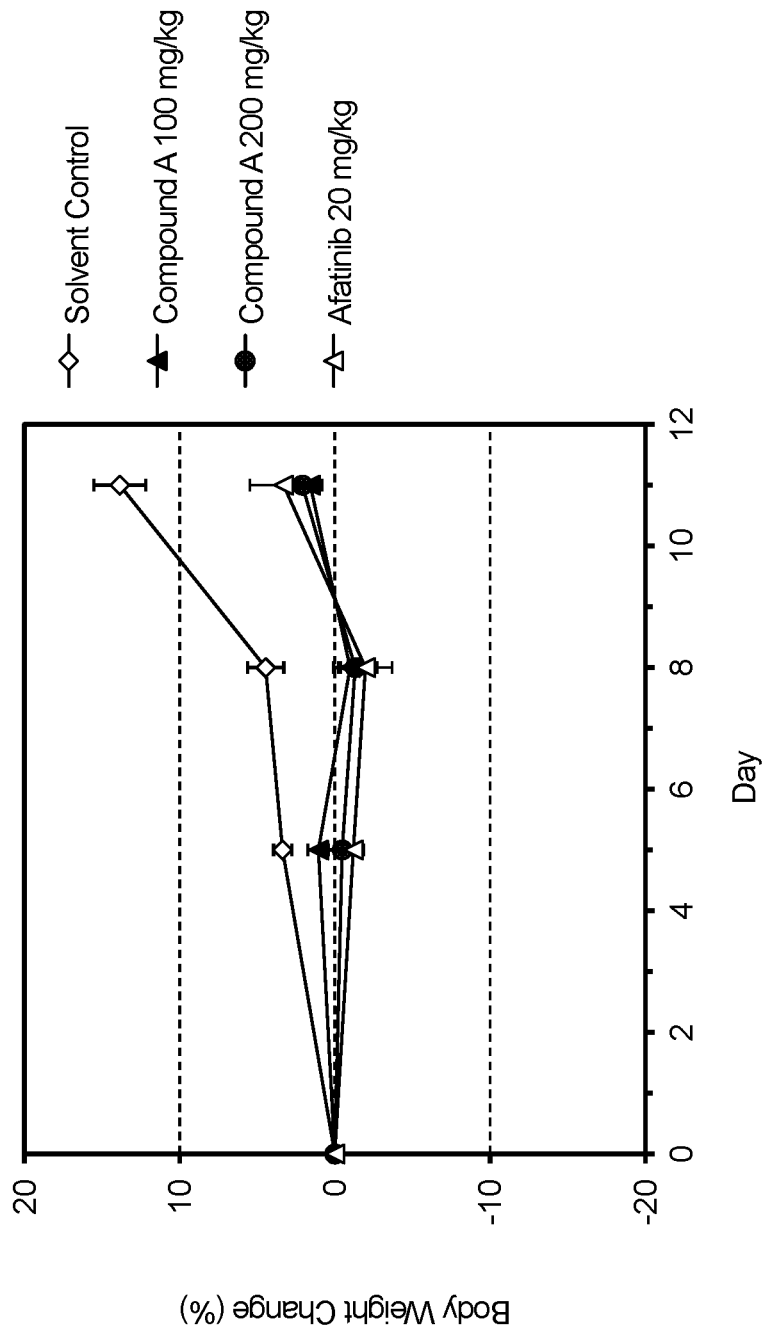
FIG. 10 illustrates the body weight after grouping of mouse models that were subcutaneously transplanted with mutant EGFR-expressing cell lines (NIH3T3-EGFRinsNPH) to measure the toxicity of compound A.

To compare the changes in growth of tumor over time due to administration of the individual test compounds, the tumor volume (which hereinafter also referred to as "TV") of each mouse was calculated using the following formula. For a toxicity index, the body weight was measured over time, and the body weight change (which hereinafter also referred to as "BWC (%)") from the day on which the mice were divided into groups was calculated in accordance with the following formula. FIGS. 9 and 10 illustrate changes in the average TV and the average BWC of the mice.
TV (mm$^3$)=(the major axis x the short axis$^2$)/2
BWC (%)=(the body weight measured on body weight measurement day)/(the body weight on the day mice were divided into groups)

When the average TV of the group administered with compound A on the day following the final administration was smaller than the average TV of the control group, while also exhibiting a statistically significant difference (Dunnett's test, p<0.05), compound A was determined to be effective in antitumor effect. Such a case is indicated by the symbol "*" in the figures. The T/C (%) on the final evaluation day was calculated in accordance with the following formula. Table 5 illustrates the results.
T/C (%)=(the tumor volume of the group administered with a test compound)/(the tumor volume of the control group)

TABLE 5

| Transplanted Tumor | Compound | 20 mg/kg | 200 mg/kg |
|---|---|---|---|
| NIH3T3 EGFRinsNPH | Compound A | N.D. | 2 |
| | Afatinib | 59 | N.D. |

N.D.: No data are available.

As is clear from FIGS. 9 and 10, and Table 5, compound A of the present invention exhibited a remarkable antitumor effect on cell lines expressing EGFR exon 20 insertion mutation subcutaneously transplanted into nude mice, accompanied by tumor growth inhibition or regression of tumor. In the evaluation, the mice also did not show serious weight loss.

Test Example 7

Evaluation of Antitumor Effect on Rat Model Subcutaneously Transplanted with Mutant EGFR-Expressing Cell Lines Nude rats were subcutaneously transplanted with H1975-EGFRinsSVD cells into which human mutant EGFR was introduced. At the point at which the tumor volume of the tumor engrafted in the nude rats grew to about 200 to 500 mm$^3$, the rats were allocated into groups, 6 rats for each group, by stratified randomization such that the average tumor volume between the groups was uniform. The rats were then orally administered compound A once daily for 14 consecutive days.

The dose was 20 or 40 mg/kg/day, which is less than the maximum tolerated dose (the highest dose at which the weight loss during a dosing period is less than 20%) for 14 days, a dosing period of this test. The maximum tolerated dose was determined in accordance with the "Guidelines Involving Experimental Neoplasia Proposals in Mice and Rats" of the National Cancer Institute (NCI), from a humanitarian perspective.

Figure 11:
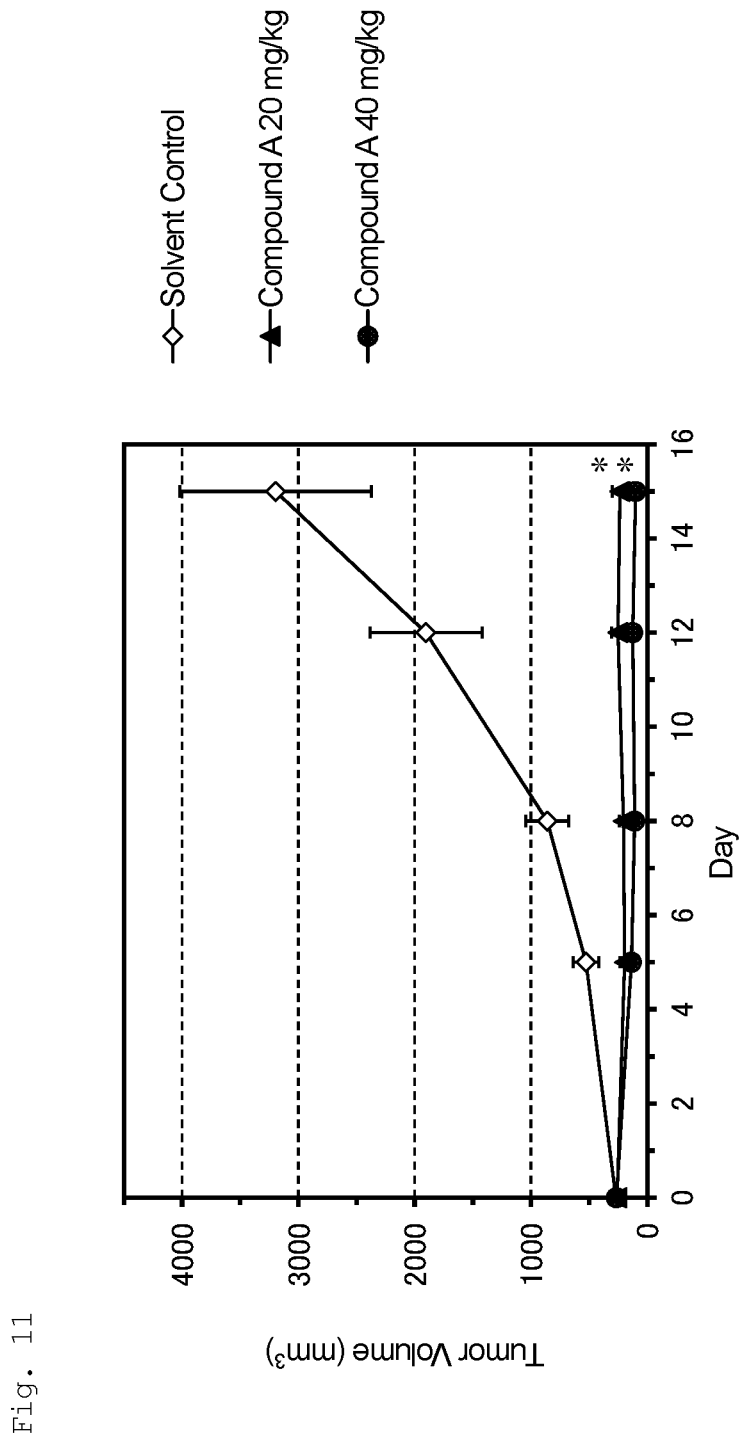
FIG. 11 illustrates the tumor volume of rat models that were subcutaneously transplanted with mutant EGFR-expressing cell lines (H1975-EGFRinsSVD cells) to measure the antitumor effect of compound A.
Figure 12:
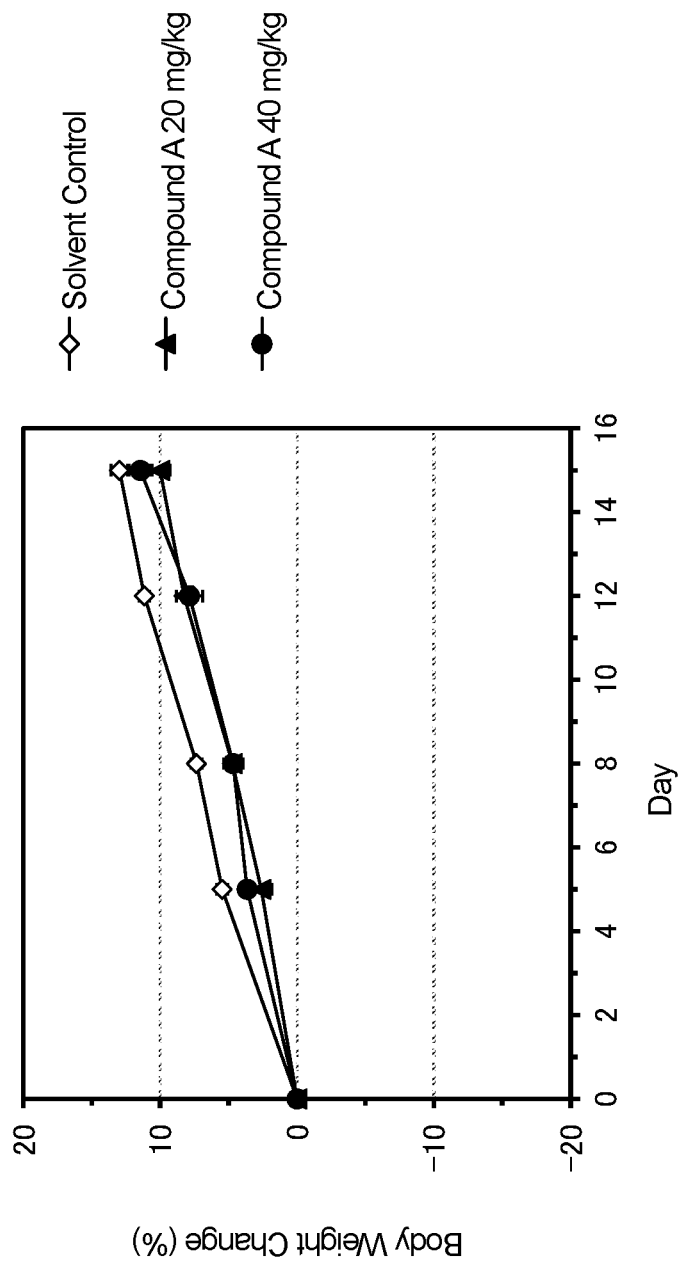
FIG. 12 illustrates the body weight after grouping of rat models that were subcutaneously transplanted with mutant EGFR-expressing cell lines (H1975-EGFRinsSVD cells) to measure the toxicity of compound A.

To compare the changes in growth of tumor over time due to administration of the test compound, the tumor volume (which hereinafter also referred to as "TV") of each rat was calculated using the following formula. For a toxicity index, the body weight was measured over time, and the body weight change (which hereinafter also referred to as "BWC (%)") from the day on which the rats were divided into groups was calculated in accordance with the following formula. FIGS. 11 and 12 illustrate changes in the average TV and the average BWC of the rats.
TV (mm$^3$)=(the major axis x the short axis$^2$)/2
BWC (%)=(the body weight measured on body weight measurement day)/(the body weight on the day rats were divided into groups)

When the average TV of the group administered with compound A on the final evaluation day was smaller than the average TV of the control group, while also exhibiting a statistically significant difference (Dunnett's test, p<0.05), compound A was determined to be effective in antitumor effect. Such a case is indicated by the symbol "*" in the figures. The T/C (%) on the final evaluation day was calculated in accordance with the following formula. Table 6 illustrates the results.

T/C (%)=(the tumor volume of the group administered with a test compound)/(the tumor volume of the control group)

TABLE 6

| Transplanted Tumor | Compound | 20 mg/kg | 40 mg/kg |
|---|---|---|---|
| H1975 EGFRinsSVD | Compound A | 7 | 3 |

As is clear from FIGS. 11 and 12, and Table 6, compound A exhibited a remarkable antitumor effect on cell lines expressing EGFR exon 20 insertion mutation subcutaneously transplanted into nude rats, accompanied by tumor growth inhibition or regression of tumor. In the evaluation, the rats did not show serious weight loss.

Test Example 8

Evaluation of Antitumor Effect on Mouse Model Subcutaneously Transplanted with Tumor Derived from Mutant EGFR-Positive Lung Cancer Patient Nude mice were subcutaneously transplanted with LXF 2478, which is a tumor derived from a human lung cancer patient who was positive for EGFR with mutation V769_D770insASV. At the point at which the tumor volume of the tumor engrafted in the nude mice grew to about 100 to 200 mm$^3$, the mice were allocated into groups, 8 mice for each group, by stratified randomization such that the average tumor volume between the groups was uniform. The mice were then orally administered compound A or afatinib once daily for 28 consecutive days, and a two-week observation period was set.

The dose of afatinib was 20 mg/kg/day, which is the maximum tolerated dose (the highest dose at which the weight loss during a dosing period is less than 20%); and the dose of compound A was 100, and 200 mg/kg/day. The maximum tolerated dose was determined in accordance with the "Guidelines Involving Experimental Neoplasia Proposals in Mice and Rats" of the National Cancer Institute (NCI), from a humanitarian perspective.

Figure 13:
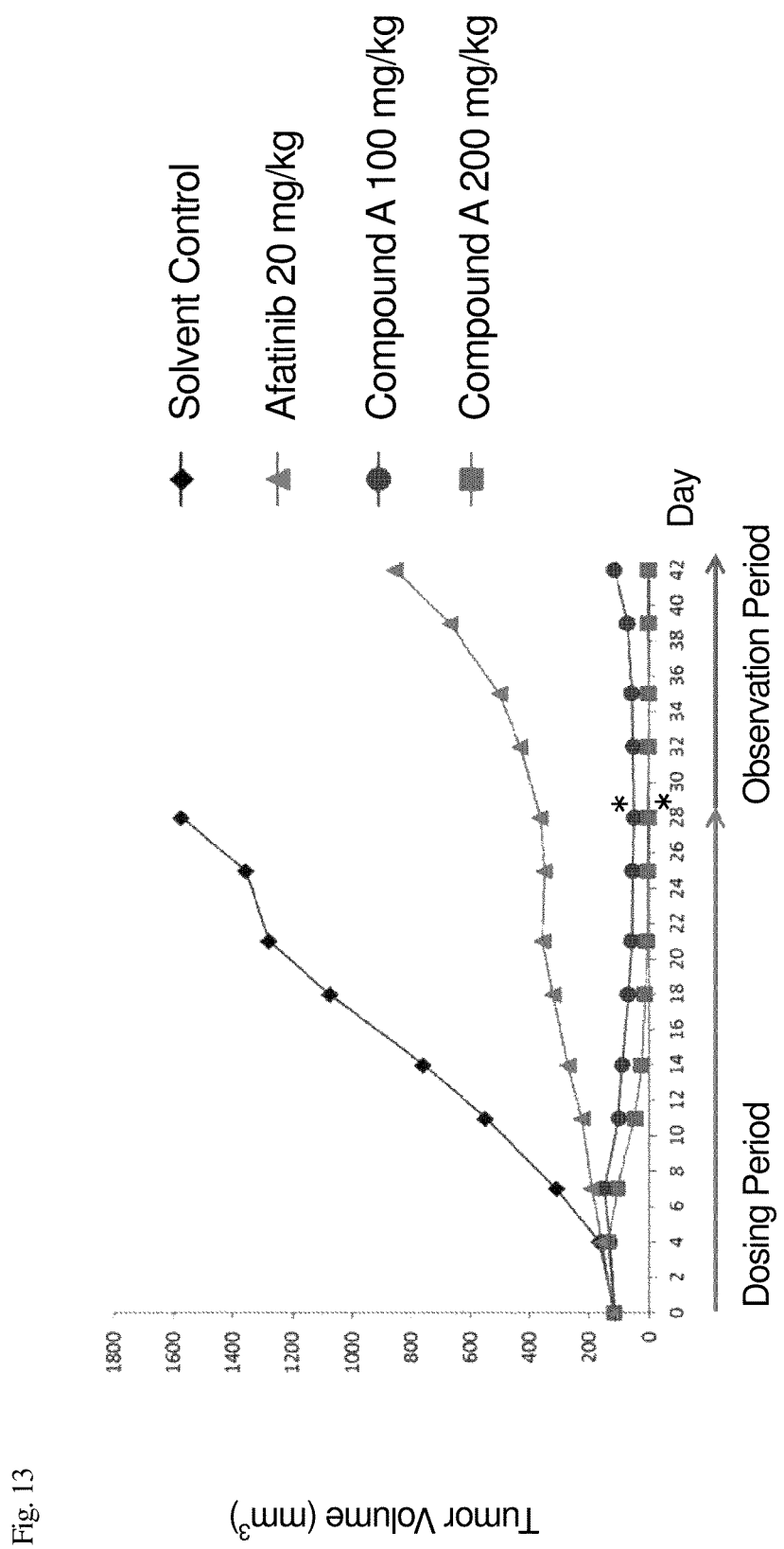
FIG. 13 illustrates the tumor volume of mouse models that were subcutaneously transplanted with a tumor derived from a lung cancer patient who was positive for EGFR with mutation V769_D770insASV to measure the antitumor effect of compound A.
Figure 14:
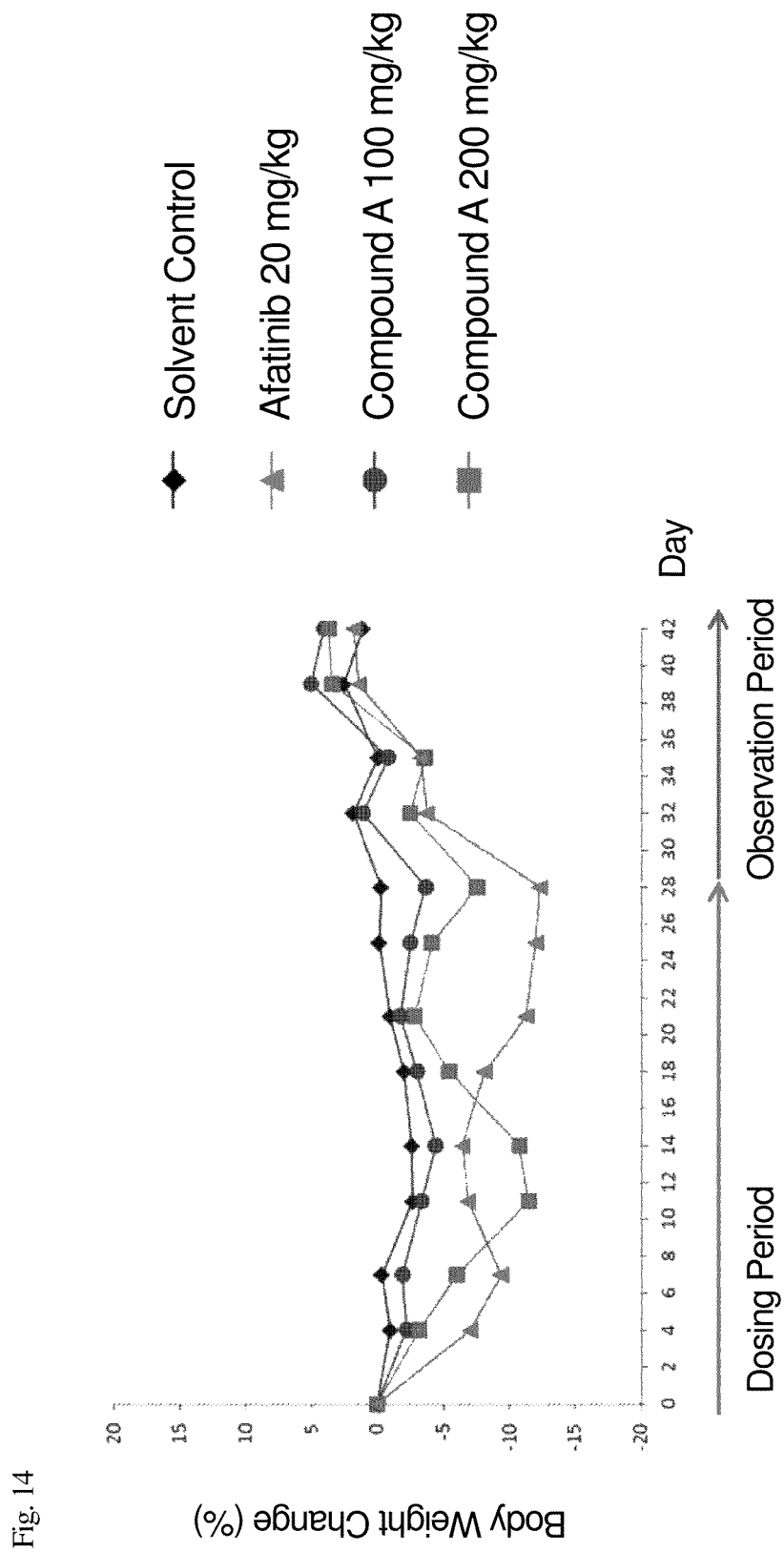
FIG. 14 illustrates the body weight after grouping of mouse models that were subcutaneously transplanted with a tumor derived from a lung cancer patient who was positive for EGFR with mutation V769_D770insASV to measure the toxicity of compound A of the present invention.

To compare the changes in growth of tumor over time due to administration of the individual test compounds, a relative tumor volume (which hereinafter also referred to as "RTV") was calculated based on the tumor volume at the time the mice were divided into groups (which is taken as 1 for the tumor growth ratio) using the following formula. For a toxicity index, the body weight was measured over time, and the body weight change (which hereinafter also referred to as "BWC (%)") from the day on which the mice were divided into groups was calculated in accordance with the following formula. FIGS. 13 and 14 illustrate changes in the average RTV and the average BWC of the mice.

RTV=(the tumor volume on the day a tumor volume was measured)/(the tumor volume on the day mice were divided into groups)

BWC (%)=(the body weight measured on body weight measurement day)/(the body weight on the day mice were divided into groups)

When the average RTV of the group administered with compound A on the day following the final administration (day 28) was smaller than the average RTV of the control group, while also exhibiting a statistically significant difference (Dunnett's test, p<0.05), compound A was determined to be effective. Such a case is indicated by the symbol "*" in the figures. The T/C (%) on the day following the final administration (day 28) was calculated in accordance with the following formula. Table 7 illustrates the results.

T/C (%)=(RTV of the group administered with a test compound)/(RTV of the control group)

TABLE 7

| Transplanted Tumor | Compound | 20 mg/kg | 100 mg/kg | 200 mg/kg |
|---|---|---|---|---|
| LXF2478 | Compound A | N.D. | 2.0 | 0.1 |
|  | Afatinib | 16.8 | N.D. | N.D. |

As is clear from FIGS. 13 and 14, and Table 7, compound A exhibited a remarkable antitumor effect on the tumor derived from a lung cancer patient who was positive for EGFR exon 20 insertion mutation subcutaneously transplanted into nude mice, accompanied by regression of tumor. The effect persisted over the observation period, and the mice did not show serious weight loss.

Test Example 9

Evaluation of Life-Extending Effect on Model Transplanted with Mutant EGFR-Expressing Cell Lines in Lung H1975-EGFRinsSVD-Luc strain was established by introducing a luciferase into H1975-EGFRinsSVD, which is a human mutant EGFR-introduced cell line. A pJTI (trademark) Fast DEST vector, which was prepared by encoding a Luciferase into NCI-H1975-EGFRinsSVD cells, was introduced into H1975-EGFRinsSVD-Luc cells, together with a pJTI (trademark) PhiC31 integrase expression vector, by electroporation using an Amaxa (trademark) Cell Line Nucleofector (trademark) Kit R, followed by selection using hygromycin B (Nacalai Tesque Inc.).

In evaluation of the life-extending effect, an equivalent amount of Matrigel was added to a suspension of cultured H1975-EGFRinsSVD-Luc cells to prepare a cell suspension, and the cell suspension was transplanted into the right lung of nude mice. On day 6 after transplantation, all of the living mice were administered a luciferin through the tail vein, and allocated into groups, 9 mice for each group, by stratified randomization such that the average luminescence intensity between the groups was uniform. The mice were then orally administered compound A or afatinib once daily on consecutive days. The dose of afatinib was 20 mg/kg/day, which is the maximum tolerated dose (the highest dose at which the weight loss during a dosing period is less than 20%); and the dose of compound A was 100, and 200 mg/kg/day. The maximum tolerated dose was determined in accordance with the "Guidelines Involving Experimental Neoplasia Proposals in Mice and Rats" of the National Cancer Institute (NCI), from a humanitarian perspective.

To evaluate the life-extending effect, the survival period after transplantation was observed, and the survival time of each mouse was determined. From the survival time, the median survival time (which hereinafter also referred to as "MST") of each group was calculated, and the survival period-extending effect (i.e., an increase in lifespan, which hereinafter also referred to as "I.L.S. (%)") was calculated based on MST of the control group and the group administered with a test compound, using the following formula. For a toxicity index, the body weight was measured over time, and the body weight change (which hereinafter also referred to as "BWC (%)") from the day on which the mice were divided into groups was calculated in accordance with the following formula.

I.L.S. (%)=(T/C-1)×100
T: MST of the group administered with a test compound
C: MST of the control group
BWC (%)=(the body weight measured on body weight measurement day)/(the body weight on the day mice were divided into groups)

When the MST of the group administered with compound A was larger than the MST of the control group, while exhibiting a statistically significant difference (Wilcoxon test, p<0.05), compound A was determined to be effective in a life-extending effect. Table 8 illustrates the results.

TABLE 8

| Transplanted Tumor | Compound | MST | I.L.S. (%) | p value |
|---|---|---|---|---|
| H1975 EGFR insSVD | Solvent Control | 44 | N.A. | N.A. |
| | Compound A 100 mg/kg | 70 | 59 | <0.01 |
| | Compound A 200 mg/kg | 89 | 102 | <0.01 |
| | Afatinib 20 mg/kg | 54 | 23 | N.S. |

N.A.: Analysis was not applicable.
N.S.: No significant difference was observed.

As is clear from Table 8, compound A exhibited a remarkable life-extending effect on the nude mouse models transplanted in the same part of their lung with cell lines expressing EGFR exon 20 insertion mutation. However, afatinib did not exhibit such a life-extending effect on the mouse models. The mice administered with compound A also did not show serious weight loss.

Test Example 10

Evaluation of Phosphorylated-EGFR Inhibitory Activity in Transplanted Tumor and Mouse Skin Tissue Nude mice were subcutaneously transplanted with NIH3T3-EGFRinsSVD cells into which human mutant EGFR was introduced. At the point at which the tumor volume of the tumor engrafted in the nude mice grew to about 250 to 500 mm$^3$, the mice were allocated into groups, 3 mice for each group, by stratified randomization such that the average tumor volume between the groups was uniform. The mice were then orally administered compound A or afatinib once. One hour and three hours after administration, which are respectively around the time at which the maximum blood concentration of compound A and afatinib is achieved, their tumor and skin tissue were collected. The collected tissue was subjected to flash-freezing with liquid nitrogen, and stored at -80° C. until use. The tumor and skin tissue were homogenized, with a RIPA buffer (Thermo Fisher Scientific) containing a protease inhibitor cocktail (Thermo Fisher Scientific) added, and proteins within the cells were extracted. The protein concentration was measured with a BCA protein assay kit (Thermo Fisher Scientific), and each sample was adjusted to a protein concentration suitable for measurement of phosphorylated EGFR expression. The proteins were separated by SDS-PAGE, and transferred onto a PVDF membrane. After blocking, Phospho-EGF Receptor (Tyr1068)#2234 (CST), which is a primary antibody, was diluted with a 0.1% TBS-T buffer to 1/1000, and allowed to react at 4° C. overnight. Thereafter, an HRP-labeled anti-rabbit antibody #NA9340V (GE Healthcare), which is a secondary antibody, was diluted to 1/2500 with a 5% skim milk solution adjusted with a 0.1% TBS-T buffer, and allowed to react at room temperature for 40 minutes. After reaction with ECL-Prime (GE Healthcare), detection was performed with an LAS-3000 image analyzer (GE Healthcare).

The test results reveal that compound A selectively inhibits mutant EGFR in the tumor over wild-type EGFR in the skin.

SEQUENCE LISTING

CLN-027US_SequenceListing.txt.

---

What is claimed is:

1. A method for treating a subject with a malignant lung tumor, the method comprising:
   detecting whether the malignant lung tumor expresses EGFR having a mutation of exon 20 insertion; and
   if the malignant lung tumor expresses EGFR having the mutation, administering to the subject an effective amount of an antitumor agent comprising (S)—N-(4-amino-6-methyl-5-(quinolin-3-yl)-8,9-dihydropyrimido[5,4-b]indolizin-8-yl)acrylamide or a salt thereof.

2. The method according to claim 1, wherein the mutation has one or more amino acids inserted in the exon 20 region.

3. The method according to claim 1, wherein the mutation has 1 to 7 amino acids inserted in the exon 20 region.

4. The method according to claim 1, wherein the mutation has 1 to 4 amino acids inserted in the exon 20 region.

5. The method according to claim 1, wherein the mutation is V769_D770insASV, D770_N771insSVD, D770_N771insG, H773_V774insNPH, or H773_V774insPH.

6. A method for treating a subject with a malignant lung tumor, comprising:
   detecting whether the malignant lung tumor expresses EGFR having a mutation of exon 20 insertion; and
   if the malignant lung tumor expresses EGFR having the mutation, administering to the subject an effective amount of
   (S)—N-(4-amino-6-methyl-5-(quinolin-3-yl)-8,9-dihydropyrimido[5,4-b]indolizin-8-yl)acrylamide
   or a salt thereof.

7. The method according to claim 1, wherein the antitumor agent further comprises a pharmaceutical carrier.

8. The method according to claim 1, wherein the antitumor agent comprising (S)—N-(4-amino-6-methyl-5-(quinolin-3-yl)-8,9-dihydropyrimido[5,4-b]indolizin-8-yl)acrylamide is administered.

9. The method according to claim 6, wherein (S)—N-(4-amino-6-methyl-5-(quinolin-3-yl)-8,9-dihydropyrimido[5,4-b]indolizin-8-yl)acrylamide is administered.

* * * * *

SEQUENCE LISTING

<160> NUMBER OF SEQ ID NOS: 1

<210> SEQ ID NO 1
<211> LENGTH: 1210
<212> TYPE: PRT
<213> ORGANISM: Homo sapiens

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val

```
            85                  90                  95
Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
            130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
            210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
            290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
            450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510
```

```
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
            530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
            595                 600                 605
Lys Tyr Ala Asp Ala Gly His Val Cys His Leu Cys His Pro Asn Cys
            610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
            690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
            755                 760                 765
Val Asp Asn Pro His Val Cys Arg Leu Leu Gly Ile Cys Leu Thr Ser
            770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
            835                 840                 845
Gln His Val Lys Ile Thr Asp Phe Gly Leu Ala Lys Leu Leu Gly Ala
            850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
            900                 905                 910
Lys Pro Tyr Asp Gly Ile Pro Ala Ser Glu Ile Ser Ser Ile Leu Glu
            915                 920                 925
```

```
Lys Gly Glu Arg Leu Pro Gln Pro Ile Cys Thr Ile Asp Val Tyr
    930             935             940

Met Ile Met Val Lys Cys Trp Met Ile Asp Ala Asp Ser Arg Pro Lys
945             950             955             960

Phe Arg Glu Leu Ile Ile Glu Phe Ser Lys Met Ala Arg Asp Pro Gln
                965             970             975

Arg Tyr Leu Val Ile Gln Gly Asp Glu Arg Met His Leu Pro Ser Pro
            980             985             990

Thr Asp Ser Asn Phe Tyr Arg Ala Leu Met Asp Glu Glu Asp Met Asp
        995             1000            1005

Asp Val Val Asp Ala Asp Glu Tyr Leu Ile Pro Gln Gln Gly Phe
    1010            1015            1020

Phe Ser Ser Pro Ser Thr Ser Arg Thr Pro Leu Leu Ser Ser Leu
    1025            1030            1035

Ser Ala Thr Ser Asn Asn Ser Thr Val Ala Cys Ile Asp Arg Asn
    1040            1045            1050

Gly Leu Gln Ser Cys Pro Ile Lys Glu Asp Ser Phe Leu Gln Arg
    1055            1060            1065

Tyr Ser Ser Asp Pro Thr Gly Ala Leu Thr Glu Asp Ser Ile Asp
    1070            1075            1080

Asp Thr Phe Leu Pro Val Pro Glu Tyr Ile Asn Gln Ser Val Pro
    1085            1090            1095

Lys Arg Pro Ala Gly Ser Val Gln Asn Pro Val Tyr His Asn Gln
    1100            1105            1110

Pro Leu Asn Pro Ala Pro Ser Arg Asp Pro His Tyr Gln Asp Pro
    1115            1120            1125

His Ser Thr Ala Val Gly Asn Pro Glu Tyr Leu Asn Thr Val Gln
    1130            1135            1140

Pro Thr Cys Val Asn Ser Thr Phe Asp Ser Pro Ala His Trp Ala
    1145            1150            1155

Gln Lys Gly Ser His Gln Ile Ser Leu Asp Asn Pro Asp Tyr Gln
    1160            1165            1170

Gln Asp Phe Phe Pro Lys Glu Ala Lys Pro Asn Gly Ile Phe Lys
    1175            1180            1185

Gly Ser Thr Ala Glu Asn Ala Glu Tyr Leu Arg Val Ala Pro Gln
    1190            1195            1200

Ser Ser Glu Phe Ile Gly Ala
    1205            1210
```